(12) United States Patent
Sharma et al.

(10) Patent No.: US 7,732,451 B2
(45) Date of Patent: Jun. 8, 2010

(54) NAPHTHALENE-CONTAINING MELANOCORTIN RECEPTOR-SPECIFIC SMALL MOLECULE

(75) Inventors: Shubh D. Sharma, Cranbury, NJ (US); Annette M. Shadiack, Somerset, NJ (US); Yiqun Shi, East Brunswick, NJ (US); Zhijun Wu, Plainsboro, NJ (US); Ramesh Rajpurohit, Hillsboro, NJ (US); Kevin D. Burris, Washington Crossing, PA (US); Papireddy Purma, Plainsboro, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 1094 days.

(21) Appl. No.: 11/036,282

(22) Filed: Jan. 14, 2005

(65) Prior Publication Data

US 2005/0130988 A1 Jun. 16, 2005

Related U.S. Application Data

(63) Continuation-in-part of application No. 10/837,519, filed on Apr. 30, 2004, now Pat. No. 7,456,184, and a continuation-in-part of application No. 10/762,079, filed on Jan. 21, 2004, now Pat. No. 7,354,923, and a continuation-in-part of application No. 10/761,889, filed on Jan. 21, 2004, now Pat. No. 7,326,707, said application No. 10/762,079 is a continuation-in-part of application No. PCT/US02/25574, filed on Aug. 12, 2002, said application No. 10/761,889 is a continuation-in-part of application No. PCT/US02/25574, filed on Aug. 12, 2002.

(60) Provisional application No. 60/536,606, filed on Jan. 14, 2004, provisional application No. 60/546,393, filed on Feb. 19, 2004, provisional application No. 60/559,741, filed on Apr. 5, 2004, provisional application No. 60/563,739, filed on Apr. 19, 2004, provisional application No. 60/474,497, filed on May 30, 2003, provisional application No. 60/441,139, filed on Jan. 17, 2003, provisional application No. 60/311,404, filed on Jan. 17, 2003, provisional application No. 60/467,442, filed on May 1, 2003.

(51) Int. Cl.
*A61K 31/4965* (2006.01)
*C07D 295/023* (2006.01)
(52) U.S. Cl. .................................. 514/255.01; 544/386
(58) Field of Classification Search ................. 544/386; 514/255.01
See application file for complete search history.

(56) References Cited

U.S. PATENT DOCUMENTS

| | | | |
|---|---|---|---|
| 4,239,763 A | 12/1980 | Milavec et al. |
| 4,418,923 A | 12/1983 | Halabiya |
| 4,626,549 A | 12/1986 | Molloy et al. |
| 4,680,289 A | 7/1987 | Applezweig |
| 4,711,957 A | 12/1987 | Lai |
| 4,766,125 A | 8/1988 | Van Daele |
| 4,937,267 A | 6/1990 | Holloway et al. |
| 4,938,763 A | 7/1990 | Dunn et al. |
| 4,943,578 A | 7/1990 | Naylor et al. |
| 4,968,684 A | 11/1990 | Van Daele et al. |
| 4,997,836 A | 3/1991 | Sugihara et al. |
| 5,120,713 A | 6/1992 | Mugica |
| 5,292,726 A | 3/1994 | Ashton et al. |
| 5,331,573 A | 7/1994 | Balaji et al. |
| 5,334,830 A | 8/1994 | Fukuyama et al. |
| 5,348,955 A | 9/1994 | Greenlee et al. |
| 5,464,788 A | 11/1995 | Bock et al. |
| 5,494,919 A | 2/1996 | Morriello et al. |
| 5,550,131 A | 8/1996 | Sugihara et al. |
| 5,574,031 A | 11/1996 | Abramo et al. |
| 5,579,250 A | 11/1996 | Balaji et al. |
| 5,599,809 A | 2/1997 | Hickey et al. |
| 5,639,778 A | 6/1997 | Andersson et al. |
| 5,672,602 A | 9/1997 | Burkholder et al. |
| 5,721,250 A | 2/1998 | Morriello et al. |
| 5,721,251 A | 2/1998 | Chen et al. |
| 5,736,539 A | 4/1998 | Graham et al. |

(Continued)

FOREIGN PATENT DOCUMENTS

WO WO 96/38471 12/1996

(Continued)

OTHER PUBLICATIONS

Synthetic Peptides: A User's Guide, GA Grant, editor, W.H. Freeman & Co., New York, 1992 the teachings of which are incorporated herein by reference, including the text and table set forth at pp. 11 through 24.

(Continued)

*Primary Examiner*—James O Wilson
*Assistant Examiner*—Ebenezer Sackey
(74) *Attorney, Agent, or Firm*—Stephen A. Slusher

(57) ABSTRACT

A method of modulating energy homeostasis in a mammal without eliciting a sexual response by administration of a therapeutically effective amount of a pharmaceutical composition including a melanocortin receptor compound of the formula:

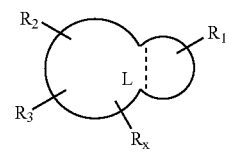

where $R_1$ is a bond or a linker unit including from one to six backbone atoms and an unsubstituted naphthalene group, and L, $R_2$, $R_3$ and $R_x$ are as defined in the specification.

15 Claims, No Drawings

U.S. PATENT DOCUMENTS

| | | |
|---|---|---|
| 5,753,445 A | 5/1998 | Fillit et al. |
| 5,753,653 A | 5/1998 | Bender et al. |
| 5,763,445 A | 6/1998 | Kruse et al. |
| 5,798,359 A | 8/1998 | Shue et al. |
| 5,804,578 A | 9/1998 | Chakravarty et al. |
| 5,856,326 A | 1/1999 | Anthony et al. |
| 5,872,262 A | 2/1999 | Dolle et al. |
| 5,877,182 A | 3/1999 | Nargund et al. |
| 5,880,125 A | 3/1999 | Nargund |
| 5,880,128 A | 3/1999 | Doll et al. |
| 5,891,418 A | 4/1999 | Sharma |
| 5,892,038 A | 4/1999 | Dolle et al. |
| 5,936,089 A | 8/1999 | Carpino et al. |
| 5,965,565 A | 10/1999 | Chen et al. |
| 5,968,938 A | 10/1999 | Williams et al. |
| 6,020,334 A | 2/2000 | Fukushi et al. |
| 6,027,711 A | 2/2000 | Sharma |
| 6,033,656 A | 3/2000 | Mikami et al. |
| 6,127,381 A | 10/2000 | Basu et al. |
| 6,127,424 A | 10/2000 | Martin et al. |
| 6,140,354 A | 10/2000 | Dax et al. |
| 6,162,805 A | 12/2000 | Hefti |
| 6,191,117 B1 | 2/2001 | Kozachuk |
| 6,207,665 B1 | 3/2001 | Bauman et al. |
| 6,207,699 B1 | 3/2001 | Rothman |
| 6,214,831 B1 | 4/2001 | Yokoo et al. |
| 6,245,764 B1 | 6/2001 | Kahn et al. |
| 6,284,735 B1 | 9/2001 | Girten et al. |
| 6,294,539 B1 | 9/2001 | Lou et al. |
| 6,303,611 B1 | 10/2001 | Zhang et al. |
| 6,316,470 B1 | 11/2001 | Kover et al. |
| 6,331,285 B1 | 12/2001 | Sharma |
| 6,340,868 B1 | 1/2002 | Lys et al. |
| 6,350,760 B1 | 2/2002 | Bakshi et al. |
| 6,372,747 B1 | 4/2002 | Taveras et al. |
| 6,376,509 B1 | 4/2002 | Bakshi et al. |
| 6,410,548 B2 | 6/2002 | Nargund et al. |
| 6,432,438 B1 | 8/2002 | Shukla |
| 6,432,959 B1 | 8/2002 | Cooper et al. |
| 6,451,783 B1 | 9/2002 | Hadcock et al. |
| 6,458,789 B1 | 10/2002 | Forood et al. |
| 6,458,790 B2 | 10/2002 | Palucki et al. |
| 6,469,006 B1 | 10/2002 | Blair et al. |
| 6,472,398 B1 | 10/2002 | Palucki et al. |
| 6,486,165 B2 | 11/2002 | Zhang et al. |
| 6,515,122 B1 | 2/2003 | Lang et al. |
| 6,531,476 B1 | 3/2003 | Heymans et al. |
| 6,534,503 B1 | 3/2003 | Dines et al. |
| 6,534,509 B1 | 3/2003 | Bauman et al. |
| 6,555,537 B2 | 4/2003 | Bauman et al. |
| 6,569,861 B2 | 5/2003 | Bakthavatchalam et al. |
| 6,579,968 B1 | 6/2003 | Blood et al. |
| 6,612,805 B2 | 9/2003 | Rietsch |
| 6,648,848 B1 | 11/2003 | Keldmann et al. |
| 6,673,767 B1 | 1/2004 | Brodbeck et al. |
| 6,699,873 B1 | 3/2004 | Maguire et al. |
| 6,715,485 B1 | 4/2004 | Djupesland |
| 6,734,175 B2 | 5/2004 | Hadcock et al. |
| 6,811,543 B2 | 11/2004 | Keldmann et al. |
| 6,949,552 B2 | 9/2005 | Nakazato et al. |
| 7,326,707 B2 | 2/2008 | Sharma et al. |
| 7,354,923 B2 | 4/2008 | Sharma et al. |
| 7,456,184 B2 | 11/2008 | Sharma et al. |
| 2001/0018075 A1 | 8/2001 | Shigeyuki et al. |
| 2001/0047001 A1 | 11/2001 | Varkhedkar et al. |
| 2002/0004512 A1 | 1/2002 | Bakshi et al. |
| 2002/0010182 A1 | 1/2002 | Masaaki et al. |
| 2002/0019523 A1 | 2/2002 | Palucki et al. |
| 2002/0022620 A1 | 2/2002 | Kahn et al. |
| 2002/0032238 A1 | 3/2002 | Priepke et al. |
| 2002/0037837 A1 | 3/2002 | Takada et al. |
| 2002/0042399 A1 | 4/2002 | Kruse et al. |
| 2002/0052383 A1 | 5/2002 | Bakthavatchalam et al. |
| 2002/0065277 A1 | 5/2002 | Hadcock et al. |
| 2002/0065416 A1 | 5/2002 | Stasiak et al. |
| 2002/0072604 A1 | 6/2002 | Carpino et al. |
| 2002/0082263 A1 | 6/2002 | Lou et al. |
| 2002/0107253 A1 | 8/2002 | Koh et al. |
| 2002/0107255 A1 | 8/2002 | Blumberg et al. |
| 2002/0128247 A1 | 9/2002 | Dow et al. |
| 2002/0128270 A1 | 9/2002 | Neya et al. |
| 2002/0137664 A1 | 9/2002 | Bakshi et al. |
| 2002/0143141 A1 | 10/2002 | Chen et al. |
| 2002/0173512 A1 | 11/2002 | Moltzen et al. |
| 2002/0177598 A1 | 11/2002 | Bauman et al. |
| 2002/0183316 A1 | 12/2002 | Pan et al. |
| 2003/0004162 A1 | 1/2003 | Treadway |
| 2003/0013721 A1 | 1/2003 | Meghani et al. |
| 2003/0040520 A1 | 2/2003 | Guzi et al. |
| 2003/0055008 A1 | 3/2003 | Marcotte |
| 2003/0055009 A1 | 3/2003 | Steiner et al. |
| 2003/0055247 A1 | 3/2003 | Cosford et al. |
| 2003/0055265 A1 | 3/2003 | Binggeli et al. |
| 2003/0060473 A1 | 3/2003 | Neya et al. |
| 2003/0064921 A1 | 4/2003 | Millhauser et al. |
| 2003/0069169 A1 | 4/2003 | Macor et al. |
| 2003/0083228 A1 | 5/2003 | Carpino et al. |
| 2003/0083335 A1 | 5/2003 | Hayward |
| 2003/0092732 A1 | 5/2003 | Yu et al. |
| 2003/0096827 A1 | 5/2003 | Yu et al. |
| 2003/0105106 A1 | 6/2003 | Chiang et al. |
| 2003/0109556 A1 | 6/2003 | Mazur et al. |
| 2003/0125334 A1 | 7/2003 | Chiang et al. |
| 2003/0139425 A1 | 7/2003 | Bauman et al. |
| 2003/0144277 A1 | 7/2003 | DeLucca |
| 2003/0149019 A1 | 8/2003 | Bremberg et al. |
| 2003/0158205 A1 | 8/2003 | Bauman et al. |
| 2003/0158209 A1 | 8/2003 | Dyck et al. |
| 2003/0162819 A1 | 8/2003 | Eisinger et al. |
| 2003/0166637 A1 | 9/2003 | Lehmann-Lintz et al. |
| 2003/0176425 A1 | 9/2003 | Eisinger et al. |
| 2003/0181441 A1 | 9/2003 | McClure et al. |
| 2003/0191136 A1 | 10/2003 | Bakthavatchalam et al. |
| 2003/0195212 A1 | 10/2003 | Lundstedt et al. |
| 2004/0006067 A1 | 1/2004 | Fotsch et al. |
| 2004/0024211 A1 | 2/2004 | Boyce et al. |
| 2004/0034034 A1 | 2/2004 | Blumberg et al. |
| 2004/0053933 A1 | 3/2004 | Pontillo et al. |
| 2004/0147567 A1 | 7/2004 | Nakazato et al. |
| 2004/0152534 A1 | 8/2004 | Chapman et al. |
| 2004/0157264 A1 | 8/2004 | Sharma et al. |
| 2004/0171520 A1 | 9/2004 | Sharma et al. |
| 2004/0204398 A1 | 10/2004 | Bakshi et al. |
| 2004/0224957 A1 | 11/2004 | Sharma et al. |
| 2004/0254198 A1 | 12/2004 | Reynolds et al. |
| 2005/0124636 A1 | 6/2005 | Sharma et al. |
| 2005/0130988 A1 | 6/2005 | Sharma et al. |
| 2005/0176728 A1 | 8/2005 | Sharma et al. |
| 2006/0009456 A1 | 1/2006 | Hutchinson et al. |
| 2006/0084657 A1 | 4/2006 | Nakazato et al. |
| 2006/0287330 A1 | 12/2006 | Sharma et al. |
| 2006/0287331 A1 | 12/2006 | Sharma et al. |
| 2006/0287332 A1 | 12/2006 | Sharma et al. |
| 2008/0070921 A1 | 3/2008 | Burris et al. |
| 2008/0234289 A1 | 9/2008 | Sharma et al. |
| 2009/0076029 A1 | 3/2009 | Sharma et al. |
| 2009/0081197 A1 | 3/2009 | Burris et al. |

FOREIGN PATENT DOCUMENTS

| | | |
|---|---|---|
| WO | WO 97/46553 | 12/1997 |
| WO | WO 98/10653 | 3/1998 |
| WO | WO 98/17625 | 4/1998 |
| WO | WO 99/55679 | 11/1999 |

| | | |
|---|---|---|
| WO | WO 99/58501 | 11/1999 |
| WO | WO 99/64002 | 12/1999 |
| WO | WO 00/01726 | 1/2000 |
| WO | WO 00/05373 | 2/2000 |
| WO | WO 00/17348 | 3/2000 |
| WO | WO 00/35952 | 6/2000 |
| WO | WO 00/36136 | 6/2000 |
| WO | WO 00/40247 | 7/2000 |
| WO | WO 00/53148 | 9/2000 |
| WO | WO 00/68185 | 11/2000 |
| WO | WO 00/74679 | 12/2000 |
| WO | WO 01/05401 | 1/2001 |
| WO | WO 01/10842 | 2/2001 |
| WO | WO 01/12176 | 2/2001 |
| WO | WO 01/13112 | 2/2001 |
| WO | WO 01/18210 | 3/2001 |
| WO | WO 01/21634 | 3/2001 |
| WO | WO 01/21647 | 3/2001 |
| WO | WO 01/23392 | 4/2001 |
| WO | WO 01/30343 | 5/2001 |
| WO | WO 01/30808 | 5/2001 |
| WO | WO 01/35970 | 5/2001 |
| WO | WO 01/52880 | 7/2001 |
| WO | WO 01/55106 | 8/2001 |
| WO | WO 01/55107 | 8/2001 |
| WO | WO 01/55109 | 8/2001 |
| WO | WO 01/70708 | 9/2001 |
| WO | WO 01/91752 | 12/2001 |
| WO | WO 02/00259 | 1/2002 |
| WO | WO 02/00654 | 1/2002 |
| WO | WO 02/12178 | 2/2002 |
| WO | WO 02/15909 | 2/2002 |
| WO | WO 02/18437 | 3/2002 |
| WO | WO 02/47670 | 6/2002 |
| WO | WO 02/059095 | 8/2002 |
| WO | WO 02/059107 | 8/2002 |
| WO | WO 02/059108 | 8/2002 |
| WO | WO 02/059117 | 8/2002 |
| WO | WO 02/062766 | 8/2002 |
| WO | WO 02/064091 | 8/2002 |
| WO | WO 02/064734 | 8/2002 |
| WO | WO 02/067869 | 9/2002 |
| WO | WO 02/068387 | 9/2002 |
| WO | WO 02/068388 | 9/2002 |
| WO | WO 02/069905 | 9/2002 |
| WO | WO 02/070511 | 9/2002 |
| WO | WO 02/079146 | 10/2002 |
| WO | WO 02/079203 | 10/2002 |
| WO | WO 02/079753 | 10/2002 |
| WO | WO 02/081443 | 10/2002 |
| WO | WO 02/085925 | 10/2002 |
| WO | WO 02/092566 | 11/2002 |
| WO | WO 03/006620 | 1/2003 |
| WO | WO 03/007949 | 1/2003 |
| WO | WO 03/009847 | 2/2003 |
| WO | WO 03/009850 | 2/2003 |
| WO | WO 03/013509 | 2/2003 |
| WO | WO 03/013571 | 2/2003 |
| WO | WO 03/020724 | 3/2003 |
| WO | WO 03/027239 | 4/2003 |
| WO | WO 03/031410 | 4/2003 |
| WO | WO 03/045920 | 6/2003 |
| WO | WO 03/053927 | 7/2003 |
| WO | WO 03/055477 | 7/2003 |
| WO | WO 03/061660 | 7/2003 |
| WO | WO 03/066587 | 8/2003 |
| WO | WO 03/066597 | 8/2003 |
| WO | WO 03/072056 | 9/2003 |
| WO | WO 03/092690 | 11/2003 |
| WO | WO 03/093234 | 11/2003 |
| WO | WO 03/094918 | 11/2003 |
| WO | WO 2004/037796 | 5/2004 |
| WO | WO 2005/102340 | 11/2005 |
| WO | WO 2006/014552 | 2/2006 |
| WO | WO 2007/021990 | 2/2007 |
| WO | WO 2007/021991 | 2/2007 |

OTHER PUBLICATIONS

Hruby VJ Al obeidi F and Kazmierski W: Biochem J 268:249-262, 1990.
Toniolo C: Int J Peptide Protein Res 35:287-300, 1990.
U.S. Appl. No. 11/110,060, filed Apr. 19, 2005, Sharma et al.
U.S. Appl. No. 12/130,299, filed May 30, 2008, Burris et al.
U.S. Appl. No. 12/130,316, filed May 30, 2008, Sharma et al.
Abou-Gharbia et al. "Synthesis and SAR of Adatanserin: Novel Adamantyl Aryl- and Heteroarylpiperazines with Dual Serotonin 5-$HT_{1a}$ and 5-$HT_2$ Activity as Potential Anxiolytic and Antidepressant Agents" J. Med. Chem. 42(25):5077-5094 (1999).
Adan et al. "Identification of antagonists for melanocortin MC3, MC4 and MC5 receptors" Eur. J. Pharmacol. 269(3):331-337 (1994).
Adan et al. "Inverse agonism gains weight" Trends in Pharmacological Sciences 24(6):315-321 (2003).
Alterman et al. "Design and synthesis of new potent C2-symmetric HIV-1 protease inhibitors. Use of L-mannaric acid as a peptidomimetic scaffold" J. Med. Chem. 41:3782-3792 (1998).
Baldwin et al. "Synthesis of a bicyclic γ-lactam dipeptide analogue" Tetrahedron Letters 34(10):1665-1668 (1993).
Chang et al. "Morphiceptin (NH4-tyr-pro-phe-pro-COHN2): a potent and specific agonist for morphine (mu) receptors" Science 212(4490):75-77 (1981).
Cho etal. "Discovery of novel, potent and orally active nonpeptide antagonist of the human luteinizing hormone-releasing hormone (LHRH) receptor" J. Med. Chem. 41:4190-4195 (1998).
Chorev et al. "Toward nonpeptidal substance P mimetic analogues: Design, synthesis, and biological activity" Biopolymers 31(6):725-733 (1991).
Cornille et al. "Anodic amide oxidations: Conformationally restricted peptide building blocks from the direct oxidation of dipeptides" Tetrahedron Letters 35(38):6989-6992 (1994).
DiMaio et al. "Synthesis of chiral piperazin-2-ones as model peptidomimetics" J Chem. Soc., Perkin Trans I, 1687-1689 (1989).
Dorr et al. "Evaluation of melanotan-II, a superpotent cyclic melanotropic peptide in a pilot phase-I clinical study" Life Science 58(20):1777-1784 (1996).
Gante "Peptidomimetics—Tailored enzyme-inhibitors" Angewandte Chemie International Edition in English 33(17):1699-1720 (1994).
Giannis et al. "Peptidomimetics in drug design" Advances in Drug Research 29:1-78 (1997).
Hadley et al. "Discovery and development of novel melanogenic drugs. Melanotan-I and -II" Ronald. T. Borchardt, et al. editors; Integration of Pharmaceutical Discovery and Development: Case Histories, Plenum Press, New York, 575-595 (1998).
Haskell-Luevano et al. "Discovery of Prototype Peptidomimetic Agonists at the Human Melanocortin Receptors MC1R and MC4R"J. Med. Chem. 40:2133-2139 (1997).
Hruby et al. "Molecular organization of receptors—Efficacy, agonists, and antagonists" Annals of the New York Academy of Sciences 757:7-22 (1995).
Jones et al. "Clinically validated peptides as templates for de novo peptidomimetic drug design at G-protein coupled receptors" Current Opinion in Pharmacology 3:530-543 (2003).
Kask et al. "Discovery of a novel superpotent and selective melanocortin-4 receptor antagonist (HS024): Evaluation in vitro and in vivo" Endocrinology 139(12):5006-5014 (1998).
Kim et al. "Synthesis of (3R)-carboxy pyrrolidine (a β-proline analogue) and its oligomer" Bioorganic & Medicinal Chemistry Letters 10(21):2417-2419 (2000).
Klein et al. "O-benzyl hydroxyproline as a bioisostere for Phe-Pro: Novel dipeptide thrombin inhibitors"Biorganic Medicinal & Chemistry Letters 6(18):2225-2230 (1996).
Lerner et al. "Synthetic melanocortin receptor. Agonist and antagonists" Cutaneous Neuroimmunomodulation: The Proopiomelanocortin System, Annals of the New York Academy of Sciences 885:153-160 (1995).

Medical Encyclopaedia: Female sexual dysfunction [online]. Retrieved on Oct. 10, 2007 from http://www.nlm.nih.gov/medlineplus/ency/article/003151.htm.

Mitsunobu "The use of diethyl azodicarboxylate and triphenylphosphine in synthesis and transfromation of natural products" Synthesis 1:1-28 (1981).

Moore et al. "A rapid screening system to determine drug affinities for the instestinal dipeptide transporter 2: Affinities of ACE inhibitors" International Journal of Pharmaceutics 210: 29-44 (2000).

Moore et al. "Designing Peptide Mimetics" Trends Pharmacol. Sci. 15:124-129 (1994).

Rarey et al. "Similarity searching in large combinatorial chemistry spaces" J. Computer-Aided Mol. Des. 15(6):497-520 (2001).

Rubsam et al. "Synthesis of chiral piperazinones as versatile scaffolds for peptidomimetics" Tetrahedron 56(43):8481-8487 (2000).

Sasaki etal. "Discovery of a thieno[2,3-d]pyrimidine-2,4-dione bearing a p-methoxyureidophenyl moiety at the 6-position: A highly potent and orally bioavailable non-peptide antagonist for the human luteinizing hormone-releasing hormone receptor" J. Med. Chem. 46:113-124 (2003).

Schioth et al. "Pharmacological comparison of rat and human melanocortin 3 and 4 receptors in vitro" Regulatory Peptides 106:7-12 (2002).

Shvachkin et al. "Synthesis of analogs of the thyrotropin-releasing hormone" Journal of General Chemistry of the USSR in English Translation 43(3):686-687 (1973).

Stavropoulos et al. "Synthesis of cis-4-hydroxy-L-proline and its incorporation into biologically important peptides" Review of Clinical Pharmacology and Pharmacokinetics 103-106 (1995).

Sudoh et al. "Transport characteristics of peptidomimetics. Effect of the pyrrolinone biostere of transport across caco-2 cell monolayers" Pharmaceutical Research 15(5):719-725 (1998).

Takenaka et al. "Synthesis of met- and leu-enkephalin analogues containing chiral N,N-ethylene-bridged phenylalanyl-methionine and -leucine" J Chem. Soc., Perkin Trans I, 8:933-937 (1993).

Torres et al. "Neoglycopeptide synthesis and purification in multi-gram scale: preparation of O-(2,3,4,6-tetra-O-acetyl-beta-D-galactopyranosyl)-N alpha-fluoren-9-yl-methoxycarbonyl-hydroxyproline and its use in the pilot-scale synthesis of the potent analgesic glycopeptide O1.5-beta-D-galactopyranosyl [DMet2, Hyp5]enkephalinamide." Journal of Peptide Science 3(2):99-109 (1997).

Torres et al. "Synthesis and conformational analysis of a series of galactosyl enkephalin analogues showing high analgesic activity" The EMBO Journal 8(10):2925-2932 (1989).

Yamamoto "Synthesis and adhesive studies of marine polypeptides" J. Chem. Soc Perkin Trans I, 3:613-618 (1987).

Zhorov et al. "Similarity of Ca2+-bound conformations of morphine and Met-enkephalin: A computational study" FEBS Letters 354(2):131-134 (1994).

Cachexia [online], retrieved on Nov. 19, 2009 from the internet (URL: http://en.wikipedia.org/wiki/Cachexia).

Inui "Cancer anorexia-cachexia syndrome: Current issues in research and management" CA A Cancer Journal for Clinicians 52:72-91 (2002).

Fan et al. "Role of melanocortinergic neurons in feeding and the agouti obesity syndrome" Nature 385(6612):165-168 (1997).

Holder et al. "Melanocortin ligands: 30 years of structure-activity relationship (SAR) studies" Medicinal Research Reviews 24(3): 325-356 (2004).

Hruby et al. "Synthesis of oligopeptide and peptidomimetic libraries" Current Opinion in Chemical Biology 1(1): 114-119 (1997).

NAPHTHALENE-CONTAINING MELANOCORTIN RECEPTOR-SPECIFIC SMALL MOLECULE

CROSS-REFERENCE TO RELATED APPLICATIONS

This application is a continuation-in-part application of U.S. patent application Ser. No. 10/762,079, entitled "Piperazine Melanocortin-Specific Compounds", filed on Jan. 21, 2004, which claimed priority to U.S. Provisional Patent Application Ser. No. 60/474,497, entitled "Substituted Piperazine Compounds Specific for Melanocortin Receptors", filed on May 30, 2003 and U.S. Provisional Patent Application Ser. No. 60/441,139, entitled "Ring Core Compounds Specific for Melanocortin Receptors", filed on Jan. 17, 2003, and which in turn was a continuation-in-part application of International Application No. PCT/US02/25574, International Publication No. WO 03/013571, entitled "Peptidomimetics of Biologically Active Metallopeptides", filed on Aug. 12, 2002, which claimed priority to U.S. Provisional Patent Application Ser. No. 60/311,404, entitled "Receptor-Specific Peptides Derived from Biologically Active Metallopeptides", filed on Aug. 10, 2001. This application is also a continuation-in-part application of U.S. patent application Ser. No. 10/761,889, entitled "Bicyclic Melanocortin-Specific Compounds", filed on Jan. 21, 2004, which claimed priority to U.S. Provisional Patent Application Ser. No. 60/441,139, entitled "Ring Core Compounds Specific for Melanocortin Receptors", filed on Jan. 17, 2003, and which in turn was a continuation-in-part application of International Application No. PCT/US02/25574, International Publication No. WO 03/013571, entitled "Peptidomimetics of Biologically Active Metallopeptides", filed on Aug. 12, 2002, which claimed priority to U.S. Provisional Patent Application Ser. No. 60/311,404, entitled "Receptor-Specific Peptides Derived from Biologically Active Metallopeptides", filed on Aug. 10, 2001. This application is also a continuation-in-part application of U.S. patent application Ser. No. 10/837,519, entitled "Melanocortin Receptor-Specific Compounds", filed on Apr. 30, 2004, which claimed priority to U.S. Provisional Patent Application Ser. No. 60/546,393, entitled "Melanocortin Receptor-Specific Tetra-Substituted Piperazine Compounds", filed on Feb. 19, 2004, and U.S. Provisional Patent Application Ser. No. 60/467,442, entitled "Tetra-, Penta- and Hexa-Substituted Piperazine Compounds and Derivatives", filed on May 1, 2003. The specification of each of the foregoing patent applications, including international applications and provisional applications, is incorporated herein by reference.

This application claims the benefit of the filing of U.S. Provisional Patent Application Ser. No. 60/536,606, entitled "Naphthalene-Containing Melanocortin Receptor-Specific Small Molecules", filed on Jan. 14, 2004; of U.S. Provisional Patent Application Ser. No. 60/546,393, entitled "Melanocortin Receptor-Specific Tetra-Substituted Piperazine Compounds", filed on Feb. 19, 2004; of U.S. Provisional Patent Application Ser. No. 60/559,741, entitled "Substituted Melanocortin Receptor-Specific Piperazine Compounds", filed on Apr. 5, 2004; and of U.S. Provisional Patent Application Ser. No. 60/563,739, entitled "Substituted Melanocortin Receptor-Specific Ketopiperazine Compounds", filed on Apr. 19, 2004; and the specification of each thereof is incorporated herein by reference.

BACKGROUND OF THE INVENTION

1. Field of the Invention (Technical Field)

The present invention relates to naphthalene-containing melanocortin receptor-specific small molecules, preferably specific for MC4-R, that are characterized in that they modulate feeding behavior in mammals without eliciting a sexual response, or significantly eliciting a sexual response, and methods for modulating feeding behavior in mammals without eliciting a sexual response, or significantly eliciting a response, by means of such MC4-R specific molecules.

2. Background Art

A family of melanocortin receptor types and subtypes have been identified, including melanocortin-1 receptors (MC1-R) expressed on normal human melanocytes and melanoma cells, melanocortin-2 receptors (MC2-R) for ACTH (adrenocorticotropin) expressed in cells of the adrenal gland, melanocortin-3 and melanocortin-4 receptors (MC3-R and MC4-R) expressed primarily in cells in the hypothalamus, midbrain and brainstem, and melanocortin-5 receptors (MC5-R), expressed in a wide distribution of tissues.

Compounds specific for MC3-R or MC4-R, and particularly MC4-R, are believed to be useful in regulation of energy homeostasis, including use as agents for attenuating food intake and body weight gain, for use in treatment of anorexia, as a weight gain aid, for treatment of obesity, and other treatment of food intake and metabolism-related disorders and conditions. Compounds specific for MC3-R and/or MC4-R, and particularly MC4-R, affect sexual response, and can be used as agents for treatment of sexual dysfunction, including male erectile dysfunction.

Because of the myriad biological effects of compounds specific for melanocortin receptors, there is a need for methods, including selection of compounds, to differentiate the effects. More specifically, the MC4-R is commonly believed to be implicated in both energy homeostasis and sexual response. For most pharmaceutical applications it is desirably to have a compound that is specific for a single biological effect, such as for example an MC4-R agonist of high affinity that regulates energy homeostasis, such as by decreasing food intake and/or body weight, without inducing a sexual response.

BRIEF SUMMARY OF THE INVENTION

Small molecules based on a ring core structure, and including as pendent groups at least a phenyl or substituted phenyl group, including but not limited to a Phe or substituted Phe side chain moiety, a $C_1$ to $C_6$ aliphatic group, a $C_1$ to $C_6$ aliphatic amino acid side chain moiety or a neutral hydrogen bonding or positively charged amino acid side chain moiety, including an Arg side chain moiety, and an unsubstituted naphthalene-containing moiety, which are agonists or partial agonists at MC4-R, decrease food intake without inducing a sexual response, including not inducing a penile erection response in male mammals. Small molecules of the defined class which are antagonists or partial antagonists at MC4-R modulate food intake without inducing a sexual response, including not inducing a penile erection response in male mammals.

The invention thus provides a method for regulating or modulating energy homeostasis, including feeding behavior, without inducing a sexual response, by administration of a therapeutically effective amount of a melanocortin-specific compound, including an MC4-R agonist compound, wherein the melanocortin-specific compound is a ring core compound with an unsubstituted naphthalene-containing pendant group.

The invention further provides, in one embodiment, melanocortin-specific compounds, including MC4-R specific compounds, which modulate energy homeostasis, including modulation of food intake, without inducing a sexual response. The invention provides both a class of compounds and method for discriminating functions heretofore associated with specificity for melanocortin receptors, including specifically MC4-R.

The invention thus provides a method of modulating energy homeostasis in a mammal without eliciting a sexual response, comprising administration of a therapeutically effective amount of a pharmaceutical composition comprising a melanocortin receptor compound of the formula:

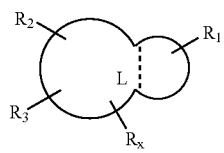

I wherein:

L is a conformationally restricted ring system consisting of a single ring or bicyclic non-aromatic carbocyclic ring system, a single ring or bicyclic aromatic carbocyclic ring system, a single ring or bicyclic non-aromatic heterocyclic ring system or a single ring or bicyclic aromatic heterocyclic ring system, with the single ring comprising from 5 to about 9 atoms, and the bicyclic ring system comprising from 5 to about 9 atoms in each ring, where the dashed line represents the common bond between shared atoms of the two rings where L is a bicyclic ring system;

$R_1$ is a bond or a linker unit comprising from one to six backbone atoms selected from the group consisting of carbon (C), oxygen (O) and nitrogen (N) and an unsubstituted naphthalene group;

$R_2$ is a $C_1$ to $C_6$ aliphatic chain and a heteroatom unit with at least one cationic center, hydrogen (H) bond donor or hydrogen bond acceptor wherein at least one heteroatom is N, a $C_1$ to $C_6$ aliphatic amino acid side chain moiety or a neutral hydrogen bonding or positively charged amino acid side chain moiety;

$R_3$ comprises a bond or a linker unit and at least one carbocyclic aromatic ring; and $R_x$ comprises from zero to about three additional pendant groups;

or an enantiomer, stereoisomer or diastereoisomer thereof, or a pharmaceutically acceptable salt thereof; and a pharmaceutically acceptable carrier.

In a preferred embodiment of the method, $R_1$ is:

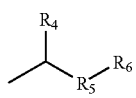

wherein:

$R_4$ is H or =O;

$R_5$ is $(CH_2)_y$, $(CH_2)_y$—O, O or NH, where y is 0 to 4; and $R_6$ is naphthalene selected from the group consisting of:

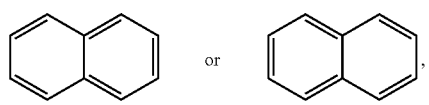

where any available carbon atom of naphthalene forms a bond with $R_5$, if provided, or the adjacent carbon atom with which $R_4$ forms a bond if $R_5$ is not provided. In a particularly preferred embodiment of the invention, $R_6$ is 2-naphthalene.

In the method, $R_2$ can be —$(CH_2)_4NH_2$, —$(CH_2)_3NHC(NH_2)$=NH, —$(CH_2)_3NHCOCH_3$, —$(CH_2)_3NHCOOCH_3$, —$(CH_2)_2NHC(NH_2)$=NH, —$(CH_2)_2NHCONH_2$, —$(CH_2)_4$ NHCOH, —$(CH_2)_4NHCOCH_3$, —$(CH_2)_3NH$-CONHCH$_3$, —$(CH_2)_3NHSO_2NH_2$, —$(CH_2)_3NHSO_2CH_3$, —$(CH_2)_3$ $NH_2$, —$(CH_2)_2CONH_2$, —$(CH_2)_3NH(C$=$NH)$ NHMe, —$(CH_2)_3NH(C$=$NH)NHEt$, —$(CH_2)_3NH$ $(C$=$NH)NHPr$, —$(CH_2)_3NH(C$=$NH)NHPr$-i, —$(CH_2)_3$ $NH(C$=$NH)NH_2$, —$(CH_2)_4NHCONH_2$, —$(CH_2)_4NH$ $(C$=$NH)NH_2$,

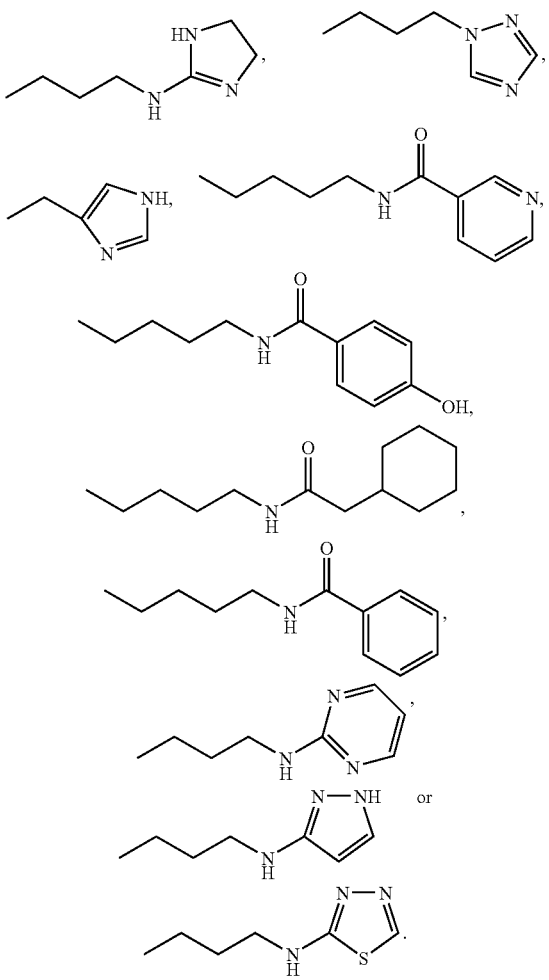

Preferably the L ring system comprises at least one nitrogen, and $R_3$ forms a bond with the at least one nitrogen. Thus $R_3$ may be an L- or D-isomer of Phe, Phe(4-F), Phe(4-Br), Phe(4-CF$_3$), Phe(4-Cl), Phe(3-Cl), Phe(2-Cl), Phe(2,4-diCl), Phe(2,4-diF), Phe(3,4-diCl), Phe(5-Cl), Phe(2-Cl,4-Me), Phe (2-Me,4-Cl), Phe(2-F,4-Cl), Phe(4-I), Phe(2,4-diMe), Phe(2-Cl,4-CF$_3$), Phe(3,4-diF), Phe(4-I), Phe(3,4-di-OMe), Phe(4-Me), Phe(4-OMe), Phe(4-NC), or Phe(4-NO$_2$). Alternatively, $R_3$ may be an L- or D-isomer of Phe, Phe(4-F), Phe(4-Br), Phe(4-CF$_3$), Phe(4-Cl), Phe(3-Cl), Phe(2-Cl), Phe(2,4-diCl), Phe(2,4-diF), Phe(3,4-diCl), Phe(5-Cl), Phe(2-Cl,4-Me), Phe (2-Me,4-Cl), Phe(2-F,4-Cl), Phe(4-I), Phe(2,4-diMe), Phe(2-Cl,4-CF$_3$), Phe(3,4-diF), Phe(4-I), Phe(3,4-di-OMe), Phe(4-

Me), Phe(4-OMe), Phe(4-NC), or Phe(4-NO$_2$) and an amine capping group. The amine capping group may be methyl, dimethyl, ethyl, propyl, isopropyl, butyl, isobutyl, pentyl, hexyl, allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7'-amino heptanoyl, 6-Ahx, Amc or 8-Aoc.

Each $R_x$ in the compound of formula I can independently be hydrogen, a $C_1$ to $C_6$ aliphatic linear or branched chain, or a bond or a linker unit comprising from one to nine backbone atoms selected from the group consisting of carbon, sulfur, oxygen or nitrogen and a group comprising at least one aromatic carbocyclic ring.

In the method, L can be a structure of any of the following formulas:

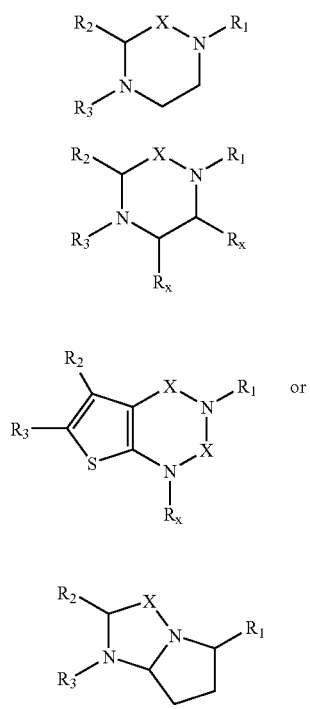

where X is independently $(CH_2)_n$, CH, NH, N, O, C=O, C=S, S, S=O or SO$_2$, n is 0, 1, 2 or 3, and $R_x$ is independently hydrogen, a $C_1$ to $C_6$ aliphatic linear or branched chain, or a bond or a linker unit comprising from one to nine backbone atoms selected from the group consisting of carbon, sulfur, oxygen and nitrogen and a group comprising at least one aromatic carbocyclic ring.

In the methods set forth in this invention, modulating energy homeostasis can include modulation of food intake. The melanocortin receptor compound employed in the methods set forth in this invention can be specific for MC4-R.

In an alternative embodiment, the invention provides a method of modulating energy homeostasis in a mammal without eliciting a sexual response, comprising administration of a therapeutically effective amount of a pharmaceutical composition comprising a melanocortin receptor compound of the formula:

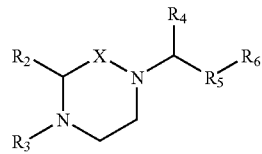

wherein:
$R_2$ is a $C_1$ to $C_6$ aliphatic chain and a heteroatom unit with at least one cationic center, hydrogen bond donor or hydrogen bond acceptor wherein at least one heteroatom is nitrogen, a $C_1$ to $C_6$ aliphatic amino acid side chain moiety or a neutral hydrogen bonding or positively charged amino acid side chain moiety;
$R_3$ comprises a bond or a linker unit and at least one carbocyclic aromatic ring;
$R_4$ is H or =O;
$R_5$ is $(CH_2)_y$, $(CH_2)_y$—O, O or NH, where y is 0 to 4; and
$R_6$ is naphthalene selected from the group consisting of:

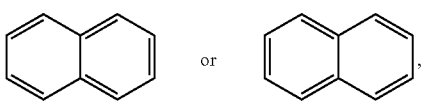

where any available carbon atom of naphthalene forms a bond with $R_5$, if provided, or the adjacent carbon atom with which $R_4$ forms a bond if $R_5$ is not provided;

X is CH$_2$, C=O, C=S, S, S=O or SO$_2$;

or an enantiomer, stereoisomer or diastereoisomer thereof, or a pharmaceutically acceptable salt thereof; and a pharmaceutically acceptable carrier. Preferably $R_6$ is 2-naphthalene.

$R_2$ can be —(CH$_2$)$_4$NH$_2$, —(CH$_2$)$_3$NHC(NH$_2$)=NH, —(CH$_2$)$_3$NHCOCH$_3$, —(CH$_2$)$_3$NHCOOCH$_3$, —(CH$_2$)$_2$NHC(NH$_2$)=NH, —(CH$_2$)$_2$NHCONH$_2$, —(CH$_2$)$_4$NHCOH, —(CH$_2$)$_4$NHCOCH$_3$, —(CH$_2$)$_3$NHCONHCH$_3$, —(CH$_2$)$_3$NHSO$_2$NH$_2$, —(CH$_2$)$_3$NHSO$_2$CH$_3$, —(CH$_2$)$_3$ NH$_2$, —(CH$_2$)$_2$CONH$_2$, —(CH$_2$)$_3$NH(C=NH)NHMe, —(CH$_2$)$_3$NH(C=NH)NHEt, —(CH$_2$)$_3$NH(C=NH)NHPr, —(CH$_2$)$_3$NH(C=NH)NHPr-i, —(CH$_2$)$_3$NH(C=NH)NH$_2$, —(CH$_2$)$_4$NHCONH$_2$, —(CH$_2$)$_4$NH(C=NH)NH$_2$,

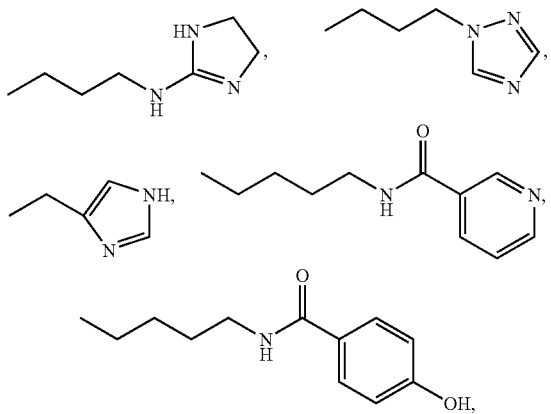

-continued

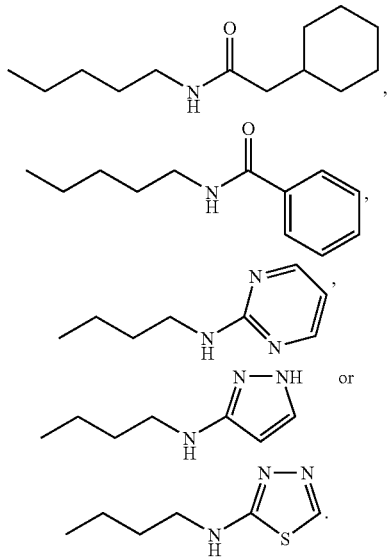

In the invention of the compound of formula VI, $R_3$ can be a D-isomer of Phe, Phe(4-F), Phe(4-Br), Phe(4-CF$_3$), Phe(4-Cl), Phe(3-Cl), Phe(2-Cl), Phe(2,4-diCl), Phe(2,4-diF), Phe(3,4-diCl), Phe(5-Cl), Phe(2-Cl,4-Me), Phe(2-Me,4-Cl), Phe(2-F,4-Cl), Phe(4-I), Phe(2,4-diMe), Phe(2-Cl,4-CF$_3$), Phe(3,4-diF), Phe(4-I), Phe(3,4-di-OMe), Phe(4-Me), Phe(4-OMe), Phe(4-NC), or Phe(4-NO$_2$). Alternatively $R_3$ can be a D-isomer of Phe, Phe(4-F), Phe(4-Br), Phe(4-CF$_3$), Phe(4-Cl), Phe(3-Cl), Phe(2-Cl), Phe(2,4-diCl), Phe(2,4-diF), Phe(3,4-diCl), Phe(5-Cl), Phe(2-Cl,4-Me), Phe(2-Me,4-Cl), Phe(2-F,4-Cl), Phe(4-I), Phe(2,4-diMe), Phe(2-Cl,4-CF$_3$), Phe(3,4-diF), Phe(4-I), Phe(3,4-di-OMe), Phe(4-Me), Phe(4-OMe), Phe(4-NC), or Phe(4-NO$_2$) and an amine capping group. The amine capping group can be methyl, dimethyl, ethyl, propyl, isopropyl, butyl, isobutyl, pentyl, hexyl, allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7'-amino heptanoyl, 6-Ahx, Amc or 8-Aoc.

In another alternative embodiment, the invention provides a method of modulating energy homeostasis in a mammal without eliciting a sexual response, comprising administration of a therapeutically effective amount of a pharmaceutical composition comprising a melanocortin receptor compound of the formula:

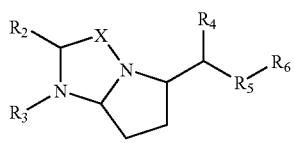

VII wherein:
$R_2$ is a $C_1$ to $C_6$ aliphatic chain and a heteroatom unit with at least one cationic center, hydrogen bond donor or hydrogen bond acceptor wherein at least one heteroatom is nitrogen, a $C_1$ to $C_6$ aliphatic amino acid side chain moiety or a neutral hydrogen bonding or positively charged amino acid side chain moiety;

$R_3$ comprises a bond or a linker unit and at least one carbocyclic aromatic ring;
$R_4$ is H or =O;
$R_5$ is $(CH_2)_y$, $(CH_2)_y$—O, O or NH, where y is 0 to 4; and
$R_6$ is naphthalene selected from the group consisting of:

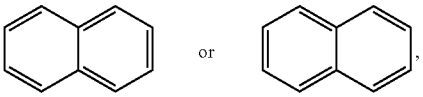

where any available carbon atom of naphthalene forms a bond with $R_5$, if provided, or the adjacent carbon atom with which $R_4$ forms a bond if $R_5$ is not provided;

X is CH$_2$, C=O, C=S, S, S=O or SO$_2$;

or an enantiomer, stereoisomer or diastereoisomer thereof, or a pharmaceutically acceptable salt thereof; and a pharmaceutically acceptable carrier. Preferably $R_6$ is 2-naphthalene.

In the method of formula VII, $R_2$ can be —(CH$_2$)$_4$NH$_2$, —(CH$_2$)$_3$NHC(NH$_2$)=NH, —(CH$_2$)$_3$NHCOCH$_3$, —(CH$_2$)$_3$NHCOOCH$_3$, —(CH$_2$)$_2$NHC(NH$_2$)=NH, —(CH$_2$)$_2$NHCONH$_2$, —(CH$_2$)$_4$NHCOH, —(CH$_2$)$_4$NHCOCH$_3$, —(CH$_2$)$_3$NHCONHCH$_3$, —(CH$_2$)$_3$NHSO$_2$NH$_2$, —(CH$_2$)$_3$NHSO$_2$CH$_3$, —(CH$_2$)$_3$NH$_2$, —(CH$_2$)$_2$CONH$_2$, —(CH$_2$)$_3$NH(C=NH)NHMe, —(CH$_2$)$_3$NH(C=NH)NHEt, —(CH$_2$)$_3$NH(C=NH)NHPr, —(CH$_2$)$_3$NH(C=NH)NHPr-i, —(CH$_2$)$_3$NH(C=NH)NH$_2$, —(CH$_2$)$_4$NHCONH$_2$, —(CH$_2$)$_4$NH(C=NH)NH$_2$,

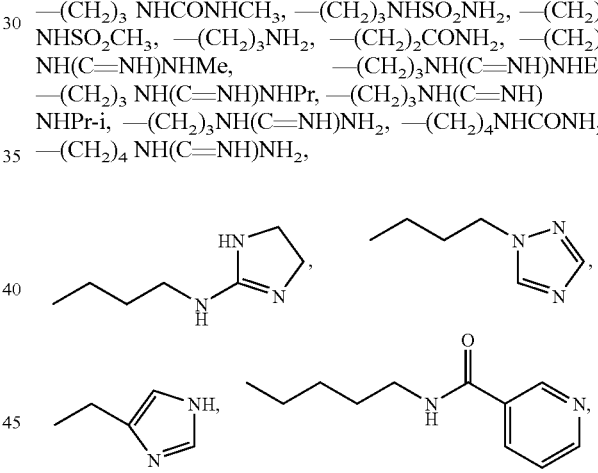

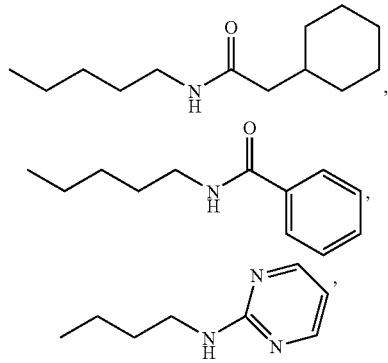

-continued

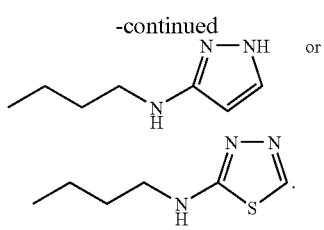

In the invention of the compound of formula VII, $R_3$ can be a D-isomer of Phe, Phe(4-F), Phe(4-Br), Phe(4-CF$_3$), Phe(4-Cl), Phe(3-Cl), Phe(2-Cl), Phe(2,4-diCl), Phe(2,4-diF), Phe(3,4-diCl), Phe(5-Cl), Phe(2-Cl,4-Me), Phe(2-Me,4-Cl), Phe(2-F,4-Cl), Phe(4-I), Phe(2,4-diMe), Phe(2-Cl,4-CF$_3$), Phe(3,4-diF), Phe(4-I), Phe(3,4-di-OMe), Phe(4-Me), Phe(4-OMe), Phe(4-NC), or Phe(4-NO$_2$). Alternatively, $R_3$ can be —$R_7$-$R_8$, where $R_7$ is a D-isomer of Phe, Phe(4-F), Phe(4-Br), Phe(4-CF$_3$), Phe(4-Cl), Phe(3-Cl), Phe(2-Cl), Phe(2,4-diCl), Phe(2,4-diF), Phe(3,4-diCl), Phe(5-Cl), Phe(2-Cl,4-Me), Phe(2-Me,4-Cl), Phe(2-F,4-Cl), Phe(4-I), Phe(2,4-diMe), Phe(2-Cl,4-CF$_3$), Phe(3,4-diF), Phe(4-I), Phe(3,4-di-OMe), Phe(4-Me), Phe(4-OMe), Phe(4-NC), or Phe(4-NO$_2$), and $R_8$ is —$R_9$, —$R_{10}$ or —$R_9$-$R_{10}$, where $R_9$ is between one and about three natural or unnatural L- or D-amino acid residues and $R_{10}$ is an amine capping group. The amine capping group can be methyl, dimethyl, ethyl, propyl, isopropyl, butyl, isobutyl, pentyl, hexyl, allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7'-amino heptanoyl, 6-Ahx, Amc or 8-Aoc.

A primary object of the present invention is to provide a compound and method for modulating feeding behavior in a mammal by means of an MC4-R specific agent without inducing a sexual response, including without inducing a penile erection response in a male.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE INVENTION

In this invention it is disclosed that ring core structures, including piperazine rings, piperazine ring derivatives, ketopiperazine rings, bicyclic rings and other ring core structures, including as pendent groups at least a phenyl or substituted phenyl group, including but not limited to a Phe or substituted Phe side chain moiety, a pendant group including $C_1$ to $C_6$ aliphatic group, a $C_1$ to $C_6$ aliphatic amino acid side chain moiety or a neutral hydrogen bonding or positively charged amino acid side chain moiety, including an Arg side chain moiety, and a pendant group including an unsubstituted naphthalene-containing moiety, may be employed to modulating energy homeostasis, including decreasing food intake and/or decreasing body weight, in a mammal without eliciting a sexual response. Heretofore, most melanocortin receptor-specific compounds, and particularly compounds which are agonists or partial agonists at MC4-R, that modulate energy homeostasis, including decreasing food intake, also induce a sexual response, including inducing a penile erection response in male mammals. Applicants have discovered that ring core compounds which include an unsubstituted naphthalene moiety do not, in general, induce a sexual response, but are nonetheless efficacious for modulating energy homeostasis. In this application, a ring core compound is said to modulate energy homeostasis, including decreasing food intake and/or decreasing body weight, without eliciting a sexual response, where at the therapeutically effective amount for modulating energy homeostasis the compound either does not induce a sexual response, or alternatively does not induce a statistically relevant sexual response.

Definitions. Before proceeding further with the description of the invention, certain terms are defined as set forth herein.

The terms "amino acid" and "amino acids" as used in the specification include the known naturally occurring protein amino acids, which are referred to by both their common three letter abbreviation and single letter abbreviation. See generally *Synthetic Peptides: A User's Guide*, G A Grant, editor, W.H. Freeman & Co., New York, 1992, the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V J, Al-obeidi F and Kazmierski W: *Biochem J* 268:249-262, 1990; and Toniolo C: *Int J Peptide Protein Res* 35:287-300, 1990; the teachings of all of which are incorporated herein by reference.

The term "amino acid side chain moiety" used in this invention, including as used in the specification and claims, includes any side chain of any amino acid, as the term "amino acid" is defined herein. This thus includes the side chain moiety present in naturally occurring amino acids. It further includes side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like. For example, the side chain moiety of any amino acid disclosed herein is included within the definition.

The "derivative" of an amino acid side chain moiety includes any modification to or variation in any amino acid side chain moieties, including a modification of naturally occurring amino acid side chain moieties. By way of example, derivatives of amino acid side chain moieties include straight chain or branched, cyclic or noncyclic, substituted or unsubstituted, saturated or unsaturated, alkyl, aryl or aralkyl moieties. Derivatives of amino acid side chain moieties further include amino acid side chain moieties, preferably amino acid side chain moieties with a functional group, the amino acid side chain moieties further including one or more protecting groups, preferably an orthogonal protecting group.

In the specification and the claims, the term "homolog" includes, without limitation, (a) a D-amino acid residue or side chain substituted for an L-amino acid residue side chain, (b) a post-translationally modified residue or side chain substituted for the residue or side chain in a parent polypeptide, (c) a non-protein or other modified amino acid residue or side chain based on such residue or side chain in a parent polypeptide, such as phenylglycine, homophenylalanine, ring-substituted halogenated, and alkylated or arylated phenylalanines for a phenylalanine residue, diamino proionic acid, diamino butyric acid, ornithine, lysine and homoarginine for an arginine residue, and the like, and (d) any amino acid residue or side chain, coded or otherwise, or a construct or structure that mimics an amino acid residue or side chain, and which has at least a similarly charged side chain (neutral, positive or negative), preferably a similar hydrophobicity or hydrophilicity, and preferably a similar side chain in terms of being a saturated aliphatic side chain, a functionalized aliphatic side chain, an aromatic side chain or a heteroaromatic side chain.

The following abbreviations for amino acids, amino acid side chain moieties and derivatives and constituents thereof have the meanings giving, it being understood that any amino acid may be in either the L- or D-configuration:

Abu—gamma-amino butyric acid
2-Abz—2-amino benzoic acid
3-Abz—3-amino benzoic acid
4-Abz—4-amino benzoic acid
Achc—1-amino-cyclohexane-1-carboxylic acid
Acpc—1-amino-cyclopropane-1-carboxylic acid
12-Ado—12-amino dodecanoic acid
Aib—alpha-aminoisobutyric acid
1-Aic—2-aminoindane-1-carboxylic acid
2-Aic—2-aminoindane-2-carboxylic acid
6-Ahx—6-amino hexanoic acid
Beta-Ala—beta-alanine
Amb—4-(aminomethyl)-benzoic acid
Amc—4-(aminomethyl)-cyclohexane carboxylic acid
7'-amino-heptanoyl—$NH_2$—$(CH_2)_6CO$—
8-Aoc—8-amino octanoic acid
Arg(Tos)—$N^G$-para-tosyl-arginine
Asp(anilino)—beta-anilino-aspartic acid
Asp(3-Cl-anilino)—beta-(3-chloro-anilino)-aspartic acid
Asp(3,5-diCl-anilino)—beta-(3,5-dichloro anilino)-aspartic acid
Atc—2-aminotetralin-2-carboxylic acid
11-Aun—11-amino undecanoic acid
AVA—5-amino valeric acid
Beta-hHyp(Bzl)—beta-(O-benzyl)-homohydroxyproline
Beta-hSer(Bzl)—beta-(O-benzyl)-homoserine
Bip—biphenylalanine
Bzl—benzyl
Bz—benzoyl
Cha—cyclohexylalanine
Chg—cyclohexylglycine
Cmpi—4-caboxymethyl-piperazine
Cys(Bzl)—S-benzyl-cysteine
Dip—3,3-diphenylalanine
Disc—1,3-dihydro-2H-isoindolecarboxylic acid
Dpr(beta-Ala)—$N^{beta}$-(3-aminopropionyl)-alpha,beta-diamino acid
Et—ethyl
GAA—epsilon-guanidino acetic acid
GBZA—4-guanidino benzoic acid
B-Gpa—3-guanidino propionic acid
GVA(Cl)—beta-chloro-epsilon-guanidino valeric acid
Heptanoyl—$CH_3$-$(CH_2)_5CO$—
hPhe—homophenylalanine
hSer—homoserine
Hyp—hydroxy proline
hHyp—homo hydroxy proline
Hyp(Bzl)—O-benzyl-hydroxyproline
Hyp(2-naphthly)—O-2' naphthyl-hydroxyproline
Hyp(Phenyl)—O-phenyl-hydroxyproline
Idc—indoline-2-carboxylic acid
Igl—indanylglycine
Inp—isonipecotic acid
Lys(Z)—N-epsilon-benzyloxycarbonyl-lysine
Me—methyl
Nal 1—3-(1-naphthyl)alanine
Nal 2—3-(2-naphthyl)alanine
(N-Bzl)Nal 2—N-benzyl-3-(2-naphthyl) alanine
2-Naphthylacetyl—2-naphthyl-$CH_2CO$—
(Nlys)Gly—N-(4-aminobutyl)-glycine
(N-PhEt)Nal 2—N(2-phenylethyl)-3-(2-naphthyl) alanine
OcHx—cyclohexyl ester
Phg—phenylglycine
Phe(4-F)—para-fluoro-phenylalanine
Phe(4-Br)—4-bromo-phenylalanine
Phe(4-$CF_3$)—4-trifluoromethyl-phenylalanine
Phe(4-Cl)—4-chloro-phenylalanine
Phe(3-Cl)—3-chloro-phenylalanine
Phe(2-Cl)—2-chloro-phenylalanine
Phe(2,4-diCl)—2,4,-dichloro-phenylalanine
Phe(2,4-diF)—2,4-difluoro-phenylalanine
Phe(3,4-diCl)—3,4,-dichloro-phenylalanine
Phe(5-Cl)—5-chloro-phenylalanine
Phe(2-Cl,4-Me)—2-chloro-4-methyl-phenylalanine
Phe(2-Me,4-Cl)—4-chloro-2-methyl-phenylalanine
Phe(2-F,4-Cl)—4-chloro-2-fluoro-phenylalanine
Phe(2,4-diMe)—2,4-dimethyl-phenylalanine
Phe(2-Cl,4-$CF_3$)—2-chloro-4-trifluoromethyl-phenylalanine
Phe(3,4-diF)—3,4,-difluoro-phenylalanine
Phe(4-I)—4-iodo-phenylalanine
Phe(3,4-di-OMe)—3,4,-dimethoxy-phenylalanine
Phe(4-Me)—4-methyl-phenylalanine
Phe(4-OMe)—4-methoxy-phenylalanine
Phe(4-NC)—4-cyano-phenylalanine
Phe(4-$NO_2$)—4-nitro-phenylalanine
Pip—pipecolic acid
Pr—propyl
Pr-i—isopropyl
4-phenylPro—4-phenyl-pyrrolidin-2-carboxylic acid
5-phenylPro—5-phenyl-pyrrolidin-2-carboxylic acid
3-Pya—3-pyridylalanine
Pyr—pyroglutamic acid
Qal(2')—beta-(2-quinolyl)-alanine
Sal—3-styrylalanine
Sar—sarcosine
Ser(Bzl) - 0-benzyl-serine
Ser(2-Naphthyl)—O-2-Naphthyl-serine
Ser(Phenyl)—O-2-Phenyl-serine
Ser(4-Cl-Phenyl)—O-4-Cl-Phenyl-serine
Ser(2-Cl-Phenyl)—O-2-Cl-Phenyl-serine
Ser(p-Cl-Bzl)—O-4-Cl-Benzyl-serine
Thr(Bzl)—O-Benzyl-threonine
Thr(2-Naphthyl)—O-(2-naphthyl)-threonine
Thr(Phenyl)—O-phenyl-threonine
Thr(4-Cl-Phenyl)—O-(4-Cl-phenyl)-threonine
Thr(2-Cl-Phenyl)—O-(2-Cl-phenyl)-threonine
Beta-homoThr(Bzl)—O-Benzyl-bate-homothreonine
Tic—1,2,3,4-tetrahydroisoquinoline-3-carboxylic acid
Tiq—1,2,3,4-tetrahydroisoquinoline-1-carboxylic acid
Tle—tert-butylalanine
Tpi—1,2,3,4-tetrahydronorharman-3-carboxylic acid
Tyr(Bzl)—O-benzyl-tyrosine
Tyr(2,6-DiCl-Bzl)—O-(2,6 dichloro)benzyl-tyrosine Conventional amino acid residues have their conventional meaning as given in Chapter 2400 of the *Manual of Patent Examining Procedure*, $8^{th}$ Ed. Thus, "His" is histidine, "D-Phe" is D-phenylalanine, "Arg" is arginine, "Trp" is tryptophan, "Tyr" is tyrosine, "Ser" is serine and so on.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "alkynal" includes a linear monovalent hydrocarbon radical of two to six carbon atoms or a branched monovalent hydrocarbon radical of three to six carbon atoms containing at least one triple bond; examples thereof include ethynyl, propynal, butynyl, and the like.

The term "aryl" includes a monovalent or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxy-carbonyl. Examples of an aryl group include phenyl, biphenyl, naphthyl, 1-naphthyl, and 2-naphthyl, derivatives thereof, and the like.

The term "aralkyl" includes a radical —$R^a R^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like.

The term "aliphatic" includes compounds with hydrocarbon chains, such as for example alkanes, alkenes, alkynes, and derivatives thereof.

The term "acyl" includes a group RCO—, where R is an organic group. An example is the acetyl group $CH_3CO$—.

A group or aliphatic moiety is "acylated" when an alkyl or substituted alkyl group as defined above is bonded through one or more carbonyl {—(C=O)—} groups.

An "omega amino derivative" includes an aliphatic moiety with a terminal amino group. Examples of omega amino derivatives include aminoheptanoyl and the amino acid side chain moieties of ornithine and lysine.

The term "heteroaryl" includes mono- and bicyclic aromatic rings containing from 1 to 4 heteroatoms selected from nitrogen, oxygen and sulfur. 5- or 6-membered heteroaryl are monocyclic heteroaromatic rings; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

An "amide" includes compounds that have a trivalent nitrogen attached to a carbonyl group (—$CO.NH_2$), such as methylamide, ethylamide, propylamide, and the like.

An "imide" includes compounds containing an imido group (—CO.NH.CO—).

An "amine" includes compounds that contain an amino group (—$NH_2$).

A "nitrile" includes compounds that are carboxylic acid derivatives and contain a (—CN) group bound to an organic group.

An amino acid side chain moiety is "hydrogen bonding" when the side chain includes hydrogen donors or alternatively hydrogen acceptors.

The term "halogen" is intended to include the halogen atoms fluorine, chlorine, bromine and iodine, and groups including one or more halogen atoms, such as —$CF_3$ and the like.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound or peptide of the present invention and a pharmaceutically acceptable carrier.

By a melanocortin receptor "agonist" is meant an endogenous or drug substance or compound that can interact with a melanocortin receptor and initiate a pharmacological response characteristic of the melanocortin receptor. By a melanocortin receptor "antagonist" is meant an endogenous or drug substance or a compound that opposes the melanocortin receptor-associated responses normally induced by a melanocortin receptor agonist agent.

By "binding affinity" is meant the ability of a compound or drug to bind to its biological target.

Formulation and Utility

The methods, compounds and pharmaceutical compositions of this invention can be used for both medical applications and animal husbandry or veterinary applications. Typically, the compound or pharmaceutical composition is used in humans, but may also be used in other mammals, particular farm or sport animals. The term "patient" is intended to denote a mammalian individual, and is so used throughout the specification and in the claims. While one primary application of this invention involves human patients, another primary application of the invention involves animals, particularly laboratory, farm, zoo, wildlife, pet, sport or other animals.

Salt Form of Compounds. The compounds of this invention may be in the form of any pharmaceutically acceptable salt. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of the compounds of this invention are prepared in a suitable solvent from the compound and an excess of an acid, such as hydrochloric, hydrobromic, sulfuric, phosphoric, acetic, trifluoroacetic, citric, tartaric, maleic, succinic or methanesulfonic acid. The acetate salt form is especially useful. Where the compounds of this invention include an acidic moiety, suitable pharmaceutically acceptable salts may include alkali metal salts, such as sodium or potassium salts, or alkaline earth metal salts, such as calcium or magnesium salts.

Pharmaceutical Compositions. The invention provides a pharmaceutical composition that includes a compound of this invention and a pharmaceutically acceptable carrier. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

The compositions of this invention may be formulated or compounded into pharmaceutical compositions that include at least one compound of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, mannitol, sodium chloride and sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a compound of this invention over a period of time.

In general, the actual quantity of compounds of this invention administered to a patient will vary between fairly wide ranges depending on the mode of administration, the formulation used, and the response desired.

In practical use, the compounds of the invention can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, buccal, sublingual, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

Because of their ease of administration, tablets and capsules represent an advantageous oral dosage unit form. If desired, tablets may be coated by standard aqueous or non-aqueous techniques. The amount of active compound in such therapeutically useful compositions is such that an effective dosage will be obtained. In another advantageous dosage unit form, sublingual constructs may be employed, such as sheets, wafers, tablets or the like. The compounds can also be administered intranasally as, for example, by liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch or alginic acid; a lubricant such as magnesium stearate; and a sweetening agent such as sucrose, lactose or saccharin. When a dosage unit form is a capsule, it may contain, in addition to materials of the above type, a liquid carrier such as fatty oil.

Various other materials may be utilized as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds may also be administered parenterally. Solutions or suspensions of compounds can be prepared in water suitably mixed with a surfactant such as hydroxy-propylcellulose. Dispersions can also be prepared in glycerol, liquid polyethylene glycols and mixtures thereof in oils. These preparations may optionally contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

The compounds of this invention may be therapeutically applied by means of nasal administration. By "nasal administration" is meant any form of intranasal administration of any of the compounds of this invention. The compounds may be in an aqueous solution, such as a solution including saline, citrate or other common excipients or preservatives. The compounds may also be in a dry or powder formulation.

In an alternative embodiment, compounds of this invention may be administered directly into the lung. Intrapulmonary administration may be performed by means of a metered dose inhaler, a device allowing self-administration of a metered bolus of a compound of this invention when actuated by a patient during inspiration.

Routes of Administration. If it is administered by injection, the injection may be intravenous, subcutaneous, intramuscular, intraperitoneal or other means known in the art. The compounds of this invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the compounds of invention are introduced across an epidermal layer of cells may be employed. Administration means may thus include administration through mucous membranes, buccal administration, oral administration, dermal administration, inhalation administration, nasal administration, urethral administration, vaginal administration, and the like.

Therapeutically Effective Amount. In general, the actual quantity of compound of this invention administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect. Thus a therapeutically effective amount includes an amount of a compound or pharmaceutical composition of this invention that is sufficient to modulate energy homeostasis, such as by increasing or decreasing food intake and/or increasing or decreasing body weight, preferably over a determined period of time.

In general, the compounds of this invention are highly active, with dose responses as low as 0.1 µg/Kg, and optimal or peak dose responses between about 0.1 µg/Kg and 25 µg/Kg, depending on the specific compound and the route of administration. For example, the compound can be administered at 0.01, 0.05, 0.1, 0.5, 1, 5, 10, 50, 100, or 500 µg/Kg body weight, depending on specific compound selected, the desired therapeutic response, the route of administration, the formulation and other factors known to those of skill in the art. Conventional dose response studies and other pharmacological means may be employed to determine the optimal dose for a desired effect with a given compound, given formulation and given route of administration.

Combination Therapy

It is also possible and contemplated to use compounds of this invention in combination with other drugs or agents. Where the compound is an agonist or partial agonist, the compound may be employed for decreasing food intake and/or body weight in combination with any other agent or drug heretofore employed as a diet aid, or for decreasing food intake and/or body weight. Where the compound is an antagonist, the compound may be employed for increasing food intake and/or body weight in combination with any other agent or drug heretofore employed for increasing food intake and/or body weight.

Drugs that reduce energy intake include, in part, various pharmacological agents, referred to as anorectic drugs, which are used as adjuncts to behavioral therapy in weight reduction programs. Classes of anorectic drugs include, but are not limited to, noradrenergic and serotonergic agents. Noradrenergic medications may be described as those medications generally preserving the anorectic effects of amphetamines but with weaker stimulant activity. The noradrenergic drugs, except phenylpropanolamine, generally act through a centrally mediated pathway in the hypothalamus that causes anorexia. Phenylpropanolamine, a racemic mixture of norephedrine esters, causes a release of norepinephrine throughout the body and stimulates hypothalamic adrenoreceptors to reduce appetite.

Suitable noradrenergic agents include, but are not limited to, diethylpropion such as TENUATE™ (1-propanone, 2-(diethylamino)-1-phenyl-, hydrochloride) commercially available from Merrell; mazindol (or 5-(p-chlorophenyl)-2,5-dihydro-3H-imidazo[2,1-a]isoindol-5-ol) such as SANOREX™ commercially available from Novartis or MAZANOR™ commercially available from Wyeth Ayerst; phenylpropanolamine (or Benzenemethanol, alpha-(1-aminoethyl)-, hydrochloride); phentermine (or Phenol, 3-[[4,5-duhydro-1H-imidazol-2-yl)ethyl](4-methylphenyl)amino], monohydrochloride) such as ADIPEX-P™, commercially available from Lemmon, FASTIN™, commercially available from Smith-Kline Beecham and Ionamin™, commercially available from Medeva; phendimetrazine (or (2S,3S)-3,4-Dimethyl-2phenylmorpholine L-(+)-tartrate (1:1)) such as METRA™, commercially available from Forest, PLEGINE™, commercially available from Wyeth-Ayerst; PRELU-2™, commercially available from Boehringer Ingelheim, and STATOBEX™, commercially available from Lemmon; phendamine tartrate such as THEPHORIN™ (2,3,4,9-Tetrahydro-2-methyl-9-phenyl-1H-indenol[2,1-c]pyridine L-(+)-tartrate (1:1)), commercially available from Hoffmann-LaRoche; methamphetamine such as DESOXYN™ Tablets ((S)—N, (alpha)-dimethylbenzeneethanamine hydrochloride) commercially available from Abbott; and phendimetrazine tartrate such as BONTRIL™ Slow-Release Capsules (-3,4-Dimethyl-2-phenylmorpholine Tartrate) commercially available from Amarin.

Suitable non-limiting serotonergic agents include sibutramine such as MERIDIA™ capsules (a racemic mixture of the (+) and (−) enantiomers of cyclobutanemethanamine, 1-(4-chlorophenyl)-N,N-dimethyl-(alpha)-(2-methylpropyl)-, hydrochloride, monohydrate) commercially available from Knoll, fenfluramine such as Pondimin™ (Benzeneethanamine, N-ethyl-alpha-methyl-3-(trifluoromethyl)-, hydrochloride) commercially available from Robbins; dexfenfluramine such as Redux™ (Benzeneethanamine, N-ethyl-alpha-methyl-3-(trifluoromethyl)-, hydrochloride) commercially available from Interneuron. Fenfluramine and dexfenfluramine stimulate release of serotonin and inhibit its reuptake. Sibutramine inhibits the reuptake of serotonin, norepinephrine and dopamine, but does not stimulate secretion of serotonin.

Other serotonergic agents useful with the practice of the present invention include, but are not limited to, certain auoretic gene 5HT1a inhibitors (brain, serotonin) such as carbidopa and benserazide as disclosed by U.S. Pat. No. 6,207,699 which is incorporated herein by reference; and certain neurokinin 1 receptor antagonist and selective serotonin reuptake inhibitors including fluoxetine, fluvoxamine, paroxtine, sertraline and other useful compounds as disclosed by U.S. Pat. No. 6,162,805 which is incorporated herein by reference. Other potential inhibitors that may be employed include 5HT2c inhibitors.

Other useful compounds for reducing energy intake include, but are not limited to, certain aryl-substituted cyclobutylalkylamines as disclosed by U.S. Pat. No. 6,127,424 which is incorporated herein by reference; certain trifluoromethylthiophenylethylamine derivatives as disclosed by U.S. Pat. No. 4,148,923 which is incorporated herein by reference; certain compounds as disclosed by U.S. Pat. No. 6,207,699 which is incorporated herein by reference; certain kainite or AMPA receptor antagonists as disclosed by U.S. Pat. No. 6,191,117 which is incorporated herein by reference;

certain neuropeptide receptor subtype 5 as disclosed by U.S. Pat. No. 6,140,354 which is incorporated herein by reference; and certain alpha-blocking agents as disclosed by U.S. Pat. No. 4,239,763 which is incorporated herein by reference.

Moreover, several peptides and hormones regulate feeding behavior. For example, cholecystokinin and serotonin act to decrease appetite and food intake. Leptin, a hormone produced by fat cells, controls food intake and energy expenditure. In obese persons who are losing weight without medications, a decrease in weight is associated with a decrease in circulating levels of leptin, suggesting its role in weight homeostasis. Obese patients with high leptin levels are thought to have peripheral leptin resistance secondary to the down-regulation of leptin receptors. Non-limiting examples of useful compounds affecting feeding behavior include certain leptin-lipolysis stimulated receptors as disclosed by WO 01/21647 which is incorporated herein by reference; certain phosphodiesterase enzyme inhibitors as disclosed by WO 01/35970 which is incorporated herein by reference; certain compounds having nucleotide sequences of the mahogany gene as disclosed by WO 00/05373 which is incorporated herein by reference; certain sapogenin compounds as disclosed by U.S. Pat. No. 4,680,289 which is incorporated herein by reference.

Other useful compounds include certain gamma peroxisome proliferator activated receptor (PPAR) agonists as disclosed by WO 01/30343 and U.S. Pat. No. 6,033,656 which are incorporated herein by reference and certain polypeptides such as fibroblast growth factor-10 polypeptides as disclosed by WO 01/18210 which is incorporated herein by reference.

Moreover, monoamine oxidase inhibitors that decrease energy intake or increase energy expenditure are useful with the practice of the present invention. Suitable, but non-limiting examples of monoamine oxidase inhibitors include befloxatone, moclobemide, brofaromine, phenoxathine, esuprone, befol, toloxatone, pirlindol, amiflamine, sercloremine, bazinaprine, lazabemide, milacemide, caroxazone and other certain compounds as disclosed by WO 01/12176 which is incorporated herein by reference.

Certain compounds that increase lipid metabolism are also useful with the practice of the present invention. Such compounds include, but are not limited to, useful evodiamine compounds as disclosed by U.S. Pat. No. 6,214,831 which is incorporated herein by reference.

Nutrient partitioning agents and digestive inhibitors are another strategy in the treatment of obesity by interfering with the breakdown, digestion or absorption of dietary fat in the gastrointestinal tract. Gastric and pancreatic lipases aid in the digestion of dietary triglycerides by forming them into free fatty acids that are then absorbed in the small intestine. Inhibition of these enzymes leads to inhibition of the digestion of dietary triglycerides. Non-limiting examples include a lipase inhibitor, orlistat, such as XENICAL™ capsules ((S)-2-formylamino-4-methyl-pentanoic acid (S)-1-[[(2S, 3S)-3-hexyl-4-oxo-2-oxetanyl]methyl]-dodecyl ester) commercially available from Roche Laboratories and certain benzoxazinone compounds as described by WO 00/40247 which is incorporated herein by reference.

Agents that increase energy expenditure are also referred to as thermogenic medications. Non-limiting examples of suitable thermogenic medications include xanthines, such as caffeine and theophylline, selective β-3-adrenergic agonists for example certain compounds in U.S. Pat. No. 4,626,549 which is incorporated by reference herein, α-2-adrenergic and growth hormones compounds as described in U.S. Pat. Nos. 4,937,267 and 5,120,713 which are incorporated by reference herein.

Generally, a total dosage of the above-described obesity control agents or medications can range from 1 to 3,000 mg/day, preferably from about 1 to 1,000 mg/day and more preferably from about 1 to 200 mg/day in single or 2-4 divided doses. The exact dose, however, is determined by the attending clinician and is dependent on such factors as the potency of the compound administered, the age, weight, condition and response of the patient.

The invention is further illustrated by the following non-limiting examples.

EXAMPLE 1

A competitive inhibition binding assay was conducted using membranes prepared from hMC3-R, hMC4-R, hMC5-R, and B-16 mouse melanoma cells (containing MC1-R) using 0.4 nM $^{125}$I-NDP-α-MSH (New England Nuclear, Boston, Mass., USA) in 50 mM HEPES buffer containing 1 mM $MgCl_2$, 2 mM $CaCl_2$, and 5 mM KCl, at pH 7.2. The assay tube also contained a chosen concentration of the test compound of this invention, for determining its efficacy in inhibiting the binding of $^{125}$I-NDP-α-MSH to its receptor. Non-specific binding was measured by complete inhibition of binding of $^{125}$I-NDP-α-MSH in the assay with the presence of 1 μM α-MSH.

Incubation was for 90 minutes at room temperature, after which the assay mixture was filtered and the membranes washed three times with ice cold buffer. The filter was dried and counted in a gamma counter for remaining radioactivity bound to the membranes. 100% specific binding was defined as the difference in radioactivity (cpm) bound to cell membranes in the absence and presence of 1 μM α-MSH. The cpm obtained in presence of test compounds were normalized with respect to 100% specific binding to determine the percent inhibition of $^{125}$I-NDP-α-MSH binding. Each assay was conducted in triplicate and the actual mean values are described. The Ki (nM) of certain compounds of the invention were determined.

EXAMPLE 2

Functional evaluation of compounds at melanocortin receptors was performed by measuring the accumulation of intracellular cAMP in HEK-293 cells expressing MC3-R, MC4-R or MC5-R, and in B-16 mouse melanoma cells (containing MC1-R). Cells, suspended in Earle's Balanced Salt Solution containing 10 mM HEPES, pH 7.5, 5 mM $MgCl_2$, 1 mM glutamine, 0.1% albumin and 0.6 mM 3-isobutyl-1-methyl-xanthine, a phosphodiesterase inhibitor, were plated in 96 well plates at a density of $0.5 \times 10^5$ cells per well. Cells were incubated with the test compounds in the presence or absence of α-MSH for 1 hour at 37° C. cAMP levels were measured by EIA (Amersham) in the cell lysates. Data analysis and $EC_{50}$ values were determined using nonlinear regression analysis with Prism Graph-Pad software.

EXAMPLE 3

The agonist/antagonist status with respect to MC4-R of certain compounds of the invention was determined. Antagonistic activity was determined by measuring the inhibition of α-MSH-induced cAMP levels following exposure to the compounds as in Example 2.

EXAMPLE 4

The ability of compounds to induce penile erection (PE) in male rats was evaluated with selected compounds. Male Sprague-Dawley rats weighing 200-250 g were kept on a 12 hour on/off light cycle with food and water ad libitum. All behavioral studies were performed between 10 a.m. and 5 p.m. Groups of 4-8 rats were treated with compounds at a variety of doses via intravenous (IV) or intracerebroventricular (ICV) routes. Immediately after treatment, rats were placed into individual polystyrene cages (27 cm long, 16 cm wide, and 25 cm high) for behavioral observation. The iv and icv treated rats were observed respectively for 30 minutes and 120 min and the number of yawns, grooming bouts and PEs were recorded in 10-minute bins.

EXAMPLE 5

Change in food intake and body weight was evaluated for selected compounds. Male Sprague-Dawley rats weighing ~300 g at the beginning of the experiment were kept on a 12 hour on/off light cycle. Lights out was adjusted to 12:00 p.m. to allow for dosing just prior to the start of their dark period. Rats (8-12/group) were fed powdered chow and water ad libitum. For 1 week before treatment, 24-hour food intake and body weight change was recorded to assess a baseline for the group during vehicle treatment. The rats were dosed ICV with vehicle or selected compounds (1-3 nmol). The changes in body weight and food intake for the 24 hour period after dosing were determined. The changes in body weight and food intake for the 48 hour period, and in same cases for 72 hours as well, after dosing were also measured to determined reversal of changes in body weight and food intake effect back to baseline.

EXAMPLE 6

Change in food intake and body weight was evaluated for selected compounds. Male Sprague-Dawley rats weighing ~300 g at the beginning of the experiment were kept on a 12 hour on/off light cycle. Lights out was adjusted to 12:00 p.m. to allow for dosing just prior to the start of their dark period. Rats (8-12/group) were fed powdered chow and water ad libitum. For 1 week before treatment, 24-hour food intake and body weight change was recorded to assess a baseline for the group during vehicle treatment. The rats were dosed IV with vehicle or selected compounds (0.5-3 mg/kg). The changes in body weight and food intake for the 24 hour period after dosing were determined. The changes in body weight and food intake for the 48 hour period, and in same cases for 72 hours as well, after dosing were also measured to determined reversal of changes in body weight and food intake effect back to baseline.

EXAMPLE 7

A compound of the following structure:

was synthesized by the general method of scheme 3 as set forth in Example 6 of WO 03/013571 and by the method of Example 1 as set forth in Example 64 of U.S. patent application Ser. No. 10/762,079, both incorporated here by reference. The molecular weight was determined to be 714.5 ESI-MS (M+1) by the method of Example 2 of WO 03/013571. ($^1$H NMR, CD$_3$OD) δ: 1.0-1.9 (m, 6H), 2.1-3.25 (m, 10H), 3.4-4.15 (m, 4H), 4.4 (m, 1H), 4.65 (m, 1H), 4.7-5.3 (m, 2H), 7.1-7.9 (m, 15H). Competitive inhibition testing of the compound against α-MSH following the methods of Example 1 yielded the following results (average of triplicates with actual mean values described; experimental results less than 0% reported as 0%):

| | Inhibition at 1 μM | | |
|---|---|---|---|
| MC1-R | MC3-R | MC4-R | MC5-R |
| 0% | 18% | 92% | 51% |

In a cAMP assay as in Example 3 for determination of agonist/antagonist status, it was determined that the compound was an agonist as to MC1-R, MC4-R and MC5-R. The Ki was determined by the method of Example 2, with the following results:

| | Ki (nM) | | |
|---|---|---|---|
| MC1-R | MC3-R | MC4-R | MC5-R |
| >1 μM | >1 μM | 50 | 789 |

In ICV feeding studies as in Example 5 at 1 nmol dose levels, a 24 hour change in food intake of −7.77 g, and change in weight of −5.88 g, was observed.

In PE studies of male rats as in Example 4, IV administration at dose levels of 0.001 to 10 μg/Kg produced no observed effect, and ICV administration at dose levels of 0.1 to 10 nmol produced no observed effect.

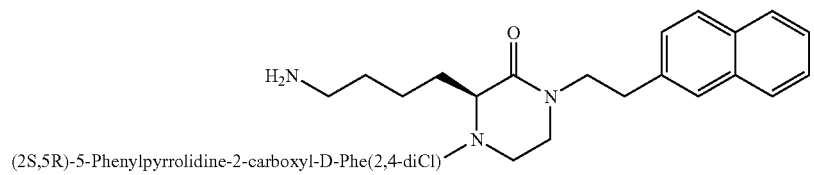

(2S,5R)-5-Phenylpyrrolidine-2-carboxyl-D-Phe(2,4-diCl)

EXAMPLE 8

A compound of the following structure:

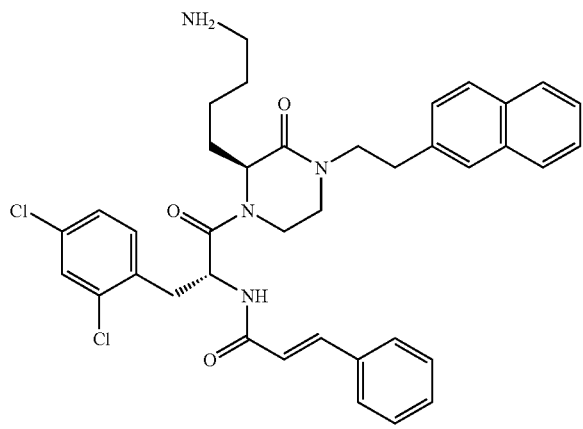

was synthesized by the general method of scheme 3 as set forth in Example 6 of WO 03/013571 and by the method of Example 1 as set forth in Example 69 of U.S. patent application Ser. No. 10/762,079, both incorporated here by reference. The molecular weight was determined to be 671.2 ESI-MS (M+1) by the method of Example 2 of WO 03/013571. ($^1$H NMR, CD$_3$OD) δ: 1.0-1.9 (m, 6H), 2.7-3.25 (m, 8H), 3.45-4.15 (m, 4H), 4.35-5.3 (m, 2H), 6.55-6.75 (m, 2H), 7.1-7.9 (m, 15H). Competitive inhibition testing of the compound against α-MSH following the methods of Example 1 yielded the following results (average of triplicates with actual mean values described):

| | Inhibition at 1 µM | | |
|---|---|---|---|
| MC1-R | MC3-R | MC4-R | MC5-R |
| 30% | 46% | 96% | 60% |

In a cAMP assay as in Example 3 for determination of agonist/antagonist status, it was determined that the compound was an antagonist as to MC1-R and MC4-R and an agonist as to MC5-R. The Ki was determined by the method of Example 2, with the following results:

| | Ki (nM) | | |
|---|---|---|---|
| MC1-R | MC3-R | MC4-R | MC5-R |
| >1 µM | >1 µM | 13 | 410 |

In ICV feeding studies as in Example 5 at 1 nmol dose levels, a 24 hour change in food intake of −10.1 g, and change in weight of −9.91 g, was observed.

In PE studies of male rats as in Example 4, IV administration at 1 µg/Kg produced a mean PE of 0.13, which is below baseline levels.

EXAMPLE 9

A compound of the following structure:

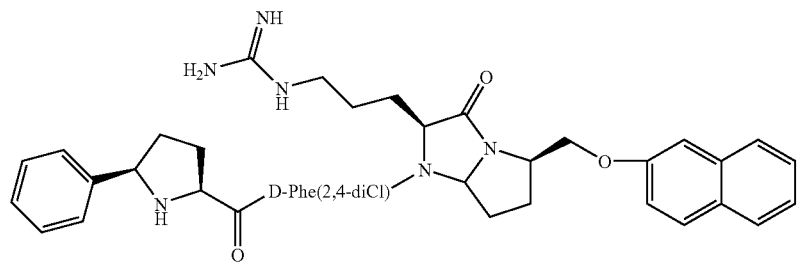

was synthesized by the general method of scheme 6 as set forth in Example 8 of WO 03/013571 and by the general method of scheme 2 of Example 1 as set forth in Example 46 of U.S. patent application Ser. No. 10/761,889, both incorporated here by reference. The molecular weight was determined to be 770.3 ESI-MS(M+1) by the method of Example 2 of WO 03/013571. ($^1$H NMR, CD$_3$OD) δ: 1.3-1.95 (m, 4H), 2.0-2.55 (m, 6H), 2.75-3.3 (m, 6H), 4.1-4.7 (m, 5H), 5.1-5.6 (m, 2H), 7.1-7.9 (m, 15H). Competitive inhibition testing of the compound against α-MSH following the methods of Example 1 yielded the following results (average of triplicates with actual mean values described):

| | Inhibition at 1 µM | | |
|---|---|---|---|
| MC1-R | MC3-R | MC4-R | MC5-R |
| 16% | 43% | 97% | 86% |

In a cAMP assay as in Example 3 for determination of agonist/antagonist status, it was determined that the compound was an agonist as to MC1-R and MC-5 and an antagonist as to MC4-R. The Ki was determined by the method of Example 2, with the following results:

| Ki (nM) | | | |
|---|---|---|---|
| MC1-R | MC3-R | MC4-R | MC5-R |
| 1041 | 312 | 12 | 99 |

In ICV feeding studies as in Example 5 at 1 nmol dose levels, a 24 hour change in food intake of −9.52 g, and change in weight of −10.64 g, was observed.

EXAMPLE 10

A compound of the following structure:

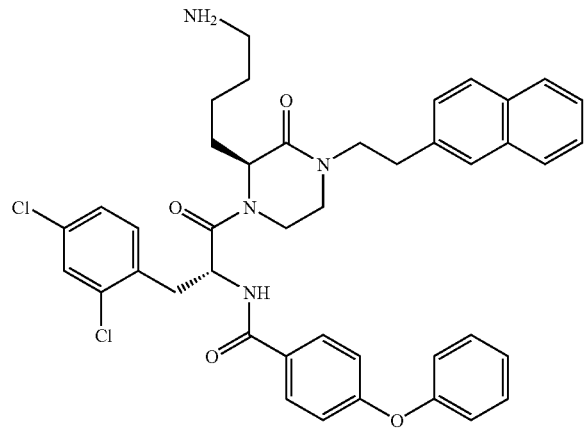

was synthesized by the general method of scheme 3 as set forth in Example 6 of WO 03/013571 and by the method of Example 1 as set forth in Example 74 of U.S. patent application Ser. No. 10/762,079, both incorporated here by reference. The molecular weight was determined to be 737.2 ESI-MS(M+1) by the method of Example 2 of WO 03/013571. ($^1$H NMR, CD$_3$OD) δ: 1.0-2.0 (m, 6H), 2.7-3.3 (m, 8H), 3.4-4.15 (m, 4H), 4.4-5.3 (m, 2H), 7.0-8.0 (m, 19H). Competitive inhibition testing of the compound against α-MSH following the methods of Example 1 yielded the following results (average of triplicates with actual mean values described):

| Inhibition at 1 μM | | | |
|---|---|---|---|
| MC1-R | MC3-R | MC4-R | MC5-R |
| 35% | 51% | 99% | 51% |

In a cAMP assay as in Example 3 for determination of agonist/antagonist status, it was determined that the compound was an antagonist as to MC1-R and MC4-R and an agonist as to MC5-R. The Ki was determined by the method of Example 2, with the following results:

| Ki (nM) | | | |
|---|---|---|---|
| MC1-R | MC3-R | MC4-R | MC5-R |
| 915 | 150 | 1 | 282 |

In ICV feeding studies as in Example 5 at 1 nmol dose levels, a 24 hour change in food intake of −0.6 g, and change in weight of −1.73 g, was observed.

In PE studies of male rats as in Example 4, IV administration at 1 μg/Kg produced a mean PE of 0.14 (below baseline), and at 50 μg/Kg a mean PE of 0.25 (not statistically relevant).

EXAMPLE 11

A compound N-{3-[1-[2(R)-Amino-3-(2,4-dichloro-phenyl)-propionyl]-5(R)-methyl-4-(2 naphthalen-2-yl-ethyl)-piperazin-2(S)-yl]-propyl}-guanidine, of the following structure:

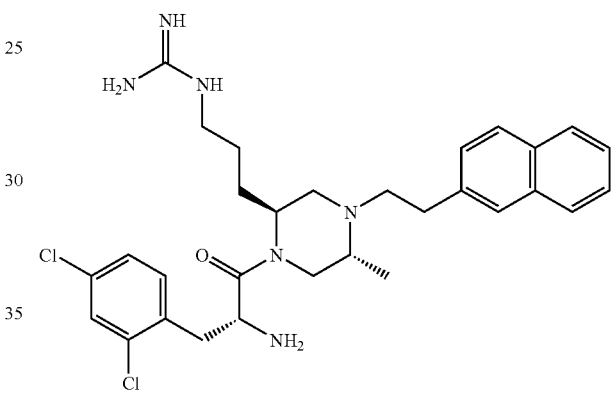

was synthesized by the methods of both Schemes 3 and 5 as set forth in Example 2 of U.S. patent application Ser. No. 10/837,519, incorporated here by reference, using 2-naphthylacetic acid as J-COOH, (R)-(−)-2-amino-1-propanol as NH$_2$—CH(R$_5$)—CH(R$_4$)—OH, Fmoc-L-Arg(Boc)$_2$-OH as Prt-NH—C(R$_2$)—COOH, D-Alanine methyl ester as NH$_2$—CH(R$_5$)—COOCH$_3$ and Boc-D-2,4-dichloro-Phe-OH as Q-COOH. Percent inhibition binding was determined as in Example 1, and yielded the following results:

| Inhibition at 1 μM | | | |
|---|---|---|---|
| MC1-R | MC3-R | MC4-R | MC5-R |
| 44% | 82% | 100% | 78% |

The Ki value was determined as in Example 2, and yielded the following results:

| Ki (nM) | | | |
|---|---|---|---|
| MC1-R | MC3-R | MC4-R | MC5-R |
| 1134 | 95 | 2 | 362 |

In a cAMP assay as in Example 3 for determination of agonist/antagonist status, it was determined that the compound was an antagonist as to MC4-R.

In ICV feeding studies as in Example 5 at 1 nmol dose levels, a 24 hour change in food intake of −2.6 g, and change in weight of −0.3 g, was observed.

EXAMPLE 12

A compound of the following structure:

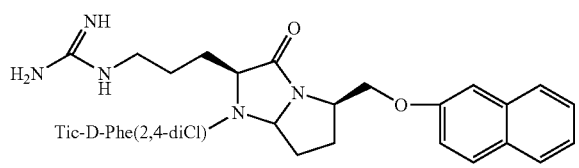

Tic-D-Phe(2,4-diCl)

was synthesized by the general method of scheme 6 as set forth in Example 8 of WO 03/013571 and the general method of scheme 2 of Example 1 as set forth in Example 43 of U.S. patent application Ser. No. 10/761,889, both incorporated here by reference. The molecular weight was determined to be 757.2 ESI-MS(M+1) by the method of Example 2 of WO 03/013571. ($^1$H NMR, CD$_3$OD) δ: 1.3-1.95 (m, 4H), 2.0-2.5 (m, 3H), 2.7-2.95 (m, 4H), 3.05-3.25 (m, 3H), 3.3 (m, 2H), 4.1-4.55 (m, 7H), 5.0-5.6 (m, 2H), 7.1-7.9 (m, 14H). Competitive inhibition testing of the compound against α-MSH following the methods of Example 1 yielded the following results (average of triplicates with actual mean values described):

| Inhibition at 1 μM | | | |
|---|---|---|---|
| MC1-R | MC3-R | MC4-R | MC5-R |
| 75% | 88% | 100% | 96% |

In a cAMP assay as in Example 3 for determination of agonist/antagonist status, it was determined that the compound was inactive as to MC1-R, and an antagonist as to MC4-R and MC5-R. The Ki was determined by the method of Example 2, with the following results:

| Ki (nM) | | | |
|---|---|---|---|
| MC1-R | MC3-R | MC4-R | MC5-R |
| 111 | 42 | 1 | 26 |

In ICV feeding studies as in Example 5 at 1 nmol dose levels, a 24 hour change in food intake of −5.4 g, and change in weight of −1.6 g, was observed.

In PE studies of male rats as in Example 4, IV administration at 1 μg/Kg produced a mean PE of 0.125, which is below baseline values.

EXAMPLE 13

A compound N-{3-[1-[2(R)-Amino-3-(2-chloro-4-methyl-phenyl)-propionyl]-5(R)-methyl-4-(2-naphthalen-2-yl-ethyl)-piperazin-2(S)-yl]-propyl}-guanidine, of the following structure:

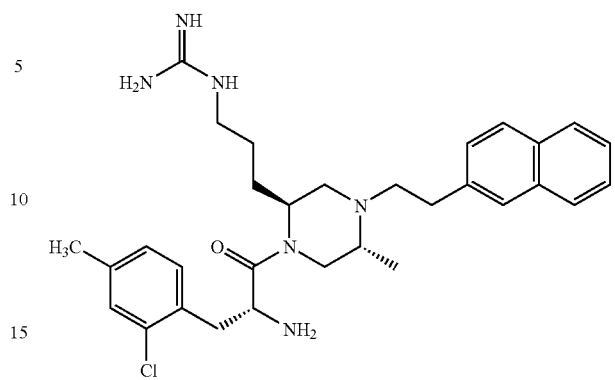

was synthesized by the methods of both Schemes 3 and 5 as set forth in Example 5 of U.S. patent application Ser. No. 10/837,519, incorporated here by reference, using 2-naphthylacetic acid as J-COOH, (R)-(−)-2-amino-1-propanol as NH$_2$—CH(R$_5$)—CH(R$_4$)—OH, Fmoc-L-Arg(Boc)$_2$-OH as Prt-NH—CH(R$_2$)—COOH, D-Alanine methyl ester as NH$_2$—CH(R$_5$)—COOCH$_3$ and Boc-D-2-chloro-4-methyl-Phe-OH as Q-COOH. Competitive inhibition testing of the compound against α-MSH following the methods of Example 1 yielded the following results (average of triplicates with actual mean values described):

| Inhibition at 1 μM | | | |
|---|---|---|---|
| MC1-R | MC3-R | MC4-R | MC5-R |
| 37% | 73% | 100% | 72% |

The Ki was determined by the method of Example 2, with the following results:

| Ki (nM) | | | |
|---|---|---|---|
| MC1-R | MC3-R | MC4-R | MC5-R |
| 907 | 227 | 5 | 527 |

In a cAMP assay as in Example 3 for determination of agonist/antagonist status, it was determined that the compound was an antagonist as to MC4-R.

In ICV feeding studies at 1 nmol dose levels as in Example 5, a 24 hour change in food intake of −1.6 g, and change in weight of −3.9 g, was observed.

EXAMPLE 14

A compound N-{3-[1-[2(R)-Amino-3-(4-chloro-2-methyl-phenyl)-propionyl]-5(R)-methyl-4-(2-naphthalen-2-yl-ethyl)-piperazin-2(S)-yl]-propyl}-guanidine, of the following structure:

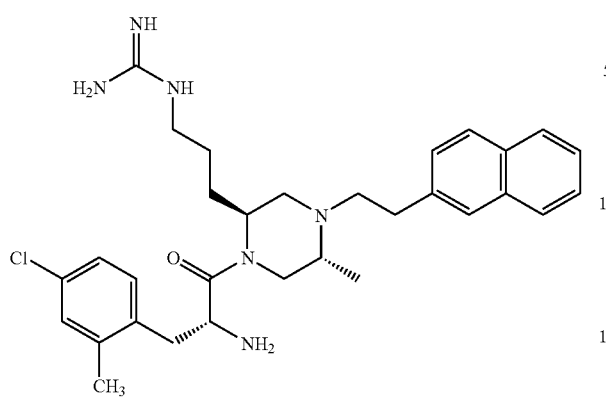
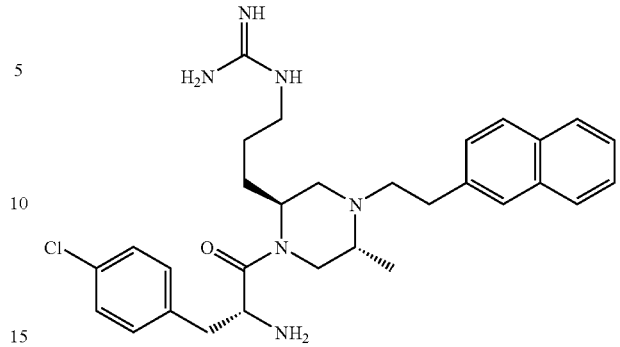

was synthesized by the methods of both Schemes 3 and 5 as set forth in Example 6 of U.S. patent application Ser. No. 10/837,519, incorporated here by reference, using 2-naphthylacetic acid as J-COOH, (R)-(−)-2-amino-1-propanol as $NH_2$—$CH(R_5)$—$CH(R_4)$—OH, Fmoc-L-Arg(Boc)$_2$-OH as Prt-NH—$CH(R_2)$—COOH, D-alanine methyl ester as $NH_2$—$CH(R_5)$—$COOCH_3$ and Boc-D-4-chloro-2-methyl-Phe-OH as Q-COOH. Competitive inhibition testing of the compound against α-MSH following the methods of Example 1 yielded the following results (average of triplicates with actual mean values described):

| Inhibition at 1 µM | | | |
|---|---|---|---|
| MC1-R | MC3-R | MC4-R | MC5-R |
| 23% | 83% | 100% | 82% |

The Ki was determined by the method of Example 2, with the following results:

| Ki (nM) | | | |
|---|---|---|---|
| MC1-R | MC3-R | MC4-R | MC5-R |
| 1052 | 99 | 1 | 219 |

In a cAMP assay as in Example 3 for determination of agonist/antagonist status, it was determined that the compound was a partial agonist as to MC4-R.

In ICV feeding studies at 1 nmol dose levels as in Example 5, a 24 hour change in food intake of −5.5 g, with no change in weight, was observed.

EXAMPLE 15

A compound N-{3-[1-[2(R)-Amino-3-(4-chloro-phenyl)-propionyl]-5(R)-methyl-4-(2-naphthalen-2-yl-ethyl)-piperazin-2(S)-yl]-propyl}-guanidine, of the following structure:

was synthesized by both the methods of both Schemes 3 and 5 as set forth in Example 12 of U.S. patent application Ser. No. 10/837,519, incorporated here by reference, using 2-naphthylacetic acid as J-COOH, D-alanine as $NH_2$—$CH(R_5)$—$CH(R_4)$—OH, D-alanine methyl ester as $NH_2$—$CH(R_5)$—$COOCH_3$, Fmoc-L-Arg(Boc)$_2$-OH as Prt-NH—$CH(R_2)$—COOH, and Boc-D-4-chloro-Phe-OH as Q-COOH. Competitive inhibition testing of the compound against α-MSH following the methods of Example 1 yielded the following results (average of triplicates with actual mean values described):

| Inhibition at 1 µM | | | |
|---|---|---|---|
| MC1-R | MC3-R | MC4-R | MC5-R |
| 85% | 61% | 97% | 52% |

The Ki was determined by the method of Example 2, with the following results:

| Ki (nM) | | | |
|---|---|---|---|
| MC1-R | MC3-R | MC4-R | MC5-R |
| 94 | 160 | 11 | 551 |

In a cAMP assay as in Example 3 for determination of agonist/antagonist status, it was determined that the compound was an agonist as to MC1-R, MC4-R and MC5-R.

In ICV feeding studies as in Example 5 at 1 nmol dose levels, a 24 hour change in food intake of −3.9 g, and change in weight of −3.9 g, was observed. In IV feeding studies as in Example 6, at a dose level of 3 µg/Kg a 24 hour change in food intake of −9.6 g and change in weight of −6.6 g was observed.

In PE studies of male rats as in Example 4, IV administration at dose levels of 0.3, 3 and 30 µg/Kg produced no observed effect.

EXAMPLE 16

A compound N-{3-[1-[2(R)-Amino-3-(2,4-dimethyl-phenyl)-propionyl]-5(R)-methyl-4-(2-naphthalen-2-yl-ethyl)-piperazin-2(S)-yl]-propyl}-guanidine, of the formula:

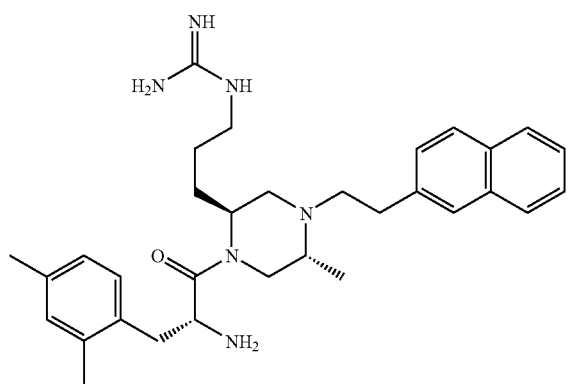

was synthesized by the methods of both Schemes 3 and 5 as set forth in Example 10 of U.S. patent application Ser. No. 10/837,519, incorporated here by reference, using 2-naphthylacetic acid as J-COOH, D-alaninol as $NH_2$—$CH(R_5)$—$CH(R_4)$—OH, D-alanine methyl ester as $NH_2$—$CH(R_5)$—$COOCH_3$, Fmoc-L-Arg(Boc)$_2$-OH as Prt-NH—$CH(R_2)$—COOH, and Boc-D-2,4-dimethyl-Phe-OH as Q-COOH. Competitive inhibition testing of the compound against α-MSH following the methods of Example 1 yielded the following results (average of triplicates with actual mean values described):

| | Inhibition at 1 μM | | |
|---|---|---|---|
| MC1-R | MC3-R | MC4-R | MC5-R |
| 22% | 67% | 98% | 73% |

The Ki was determined by the method of Example 2, with the following results:

| | Ki (nM) | | |
|---|---|---|---|
| MC1-R | MC3-R | MC4-R | MC5-R |
| 1223 | 157 | 11 | 717 |

In a cAMP assay as in Example 3 for determination of agonist/antagonist status, it was determined that the compound was an agonist as to MC4-R.

In ICV feeding studies as in Example 5 at 1 nmol dose levels, a 24 hour change in food intake of −2.6 g, and change in weight of −5 g, was observed. In IV feeding studies as in Example 6, at a dose level of 3 μg/Kg a 24 hour change in food intake of −7.3 g and change in weight of −6.3 g was observed.

EXAMPLE 17

Compounds of the formula:

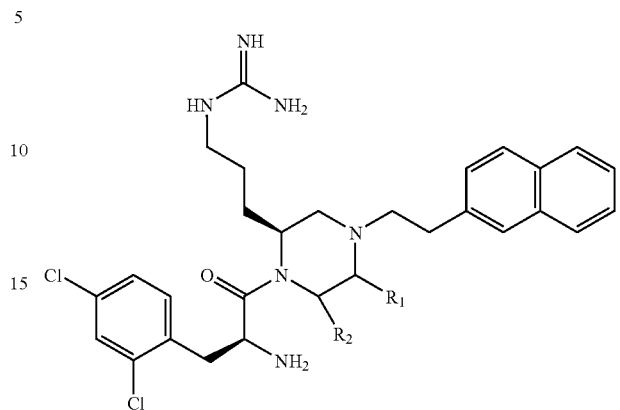

were synthesized, where $R_1$ and $R_2$ are as shown on Table 1. The compound N-{3-[1-[2(R)-Amino-3-(2,4-dichloro-phenyl)-propionyl]-6(R)-methyl-4-(2-naphthalen-2-yl-ethyl)-piperazin-2(S)-yl]-propyl}-guanidine has (R)—$CH_3$ at $R_2$, while the compound N-{3-[1-[2(R)-Amino-3-(2,4-dichloro-phenyl)-propionyl]-6(S)-methyl-4-(2-naphthalen-2-yl-ethyl)-piperazin-2(S)-yl]-propyl}-guanidine has (S)-$CH_3$ at $R_2$. The compound with (R)—$CH_3$ at $R_2$ was synthesized by the method of Scheme 3 as set forth in Example 1 of U.S. patent application Ser. No. 10/837,519, incorporated here by reference, using 2-naphthylacetic acid as J-COOH, (S)-(+)-1-amino-2-propanol as $NH_2$—$CH(R_5)$—$CH(R_4)$—OH, Fmoc-L-Arg(Boc)$_2$-OH as Prt-NH—$C(R_2)$—COOH and Boc-D-2,4-dichloro-Phe-OH as Q-COOH. The compound with (S)-$CH_3$ at $R_2$ was synthesized by the method of Scheme 3 as set forth in Example 4 of U.S. patent application Ser. No. 10/837,519, incorporated here by reference, using 2-naphthylacetic acid as J-COOH, (R)-(−)-1-amino-2-propanol as $NH_2$—$CH(R_5)$—$CH(R_4)$—OH, Fmoc-L-Arg(Boc)$_2$-OH as Prt-NH—$CH(R_2)$—COOH, and Boc-D-2,4-dichloro-Phe-OH as Q-COOH. Testing for competitive inhibition data at 1 μM was determined as in Example 1 and molecular weight was also determined.

TABLE 1

| $R_1$ | $R_2$ | MC1-R | MC3-R | MC4-R | MC5-R | (M + 1) |
|---|---|---|---|---|---|---|
| | | | % Inhibition at 1 μM | | | |
| H | (R)-$CH_3$ | 14% | 32% | 95% | 36% | 569.4 |
| H | (S)-$CH_3$ | 3% | 47% | 97% | 64% | 569.0 |

The Ki of the second compound [(S)-$CH_3$] was determined by the method of Example 2, with the following results:

| | Ki (nM) | | |
|---|---|---|---|
| MC1-R | MC3-R | MC4-R | MC5-R |
| 3185 | 551 | 21 | 602 |

In a cAMP assay as in Example 3 for determination of agonist/antagonist status, it was determined that the second compound [(S)-$CH_3$] was an agonist as to MC1-R and MC4-R, and inactive as to MC5-R.

EXAMPLE 18

A compound of the formula:

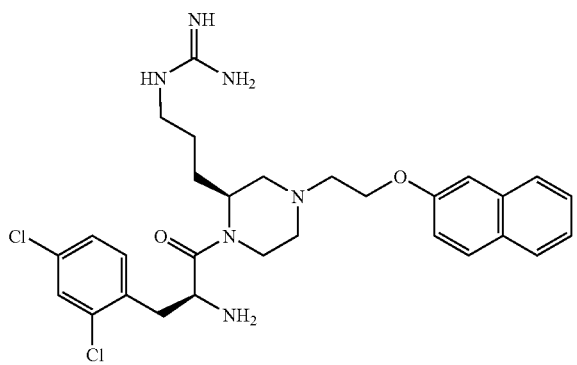

was synthesized by the methods of Example 5 as set forth in Example 92 of U.S. patent application Ser. No. 10/762,079, incorporated here by reference. The molecular weight was determined to be 571.2 ESI-MS (M+1) by the method of Example 2 of WO 03/013571. Competitive inhibition testing of the compound against α-MSH following the methods of Example 1 yielded the following results (average of triplicates with actual mean values described):

| | Inhibition at 1 μM | | |
|---|---|---|---|
| MC1-R | MC3-R | MC4-R | MC5-R |
| 25% | 33% | 91% | 40% |

The preceding examples can be repeated with similar success by substituting the generically or specifically described compositions, substituents and synthetic methods of this invention for those used in the preceding examples.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above, and of the corresponding application(s), are hereby incorporated by reference.

What is claimed is:

1. A method of decreasing food intake and/or decreasing body weight in a mammal without eliciting a sexual response, comprising administration to a mammal in need thereof of a therapeutically effective amount of a pharmaceutical composition comprising a melanocortin receptor compound of the formula:

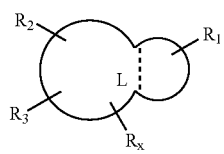

I wherein:
L is a conformationally restricted ring system consisting of a single non-aromatic heterocyclic ring system, with the single ring comprising 6 atoms;

$R_1$ is a linker unit comprising from one to six backbone atoms selected from the group consisting of carbon (C), oxygen (O) and nitrogen (N) and an unsubstituted naphthalene group;

$R_2$ is —$(CH_2)_4NH_2$, —$(CH_2)_3NHC(NH_2)$=NH, —$(CH_2)_3$ $NHCOCH_3$, —$(CH_2)_3NHCOOCH_3$, —$(CH_2)_2$ $NHC(NH_2)$=NH, —$(CH_2)_2NHCONH_2$, —$(CH_2)_4$ $NHCOH$, —$(CH_2)_4NHCOCH_3$, —$(CH_2)_3$ $NHCONHCH_3$, —$(CH_2)_3NHSO_2NH_2$, —$(CH_2)_3$ $NHSO_2CH_3$, —$(CH_2)_3NH_2$, —$(CH_2)_3NH(C$=NH) NHMe, —$(CH_2)_3$ NH(C=NH)NHEt, —$(CH_2)_3NH$ (C=NH)NHPr, —$(CH_2)_3NH(C$=NH)NHPr-i, —$(CH_2)_3NH(C$=NH)$NH_2$, —$(CH_2)_4NHCONH_2$, —$(CH_2)_4NH(C$=NH)$NH_2$,

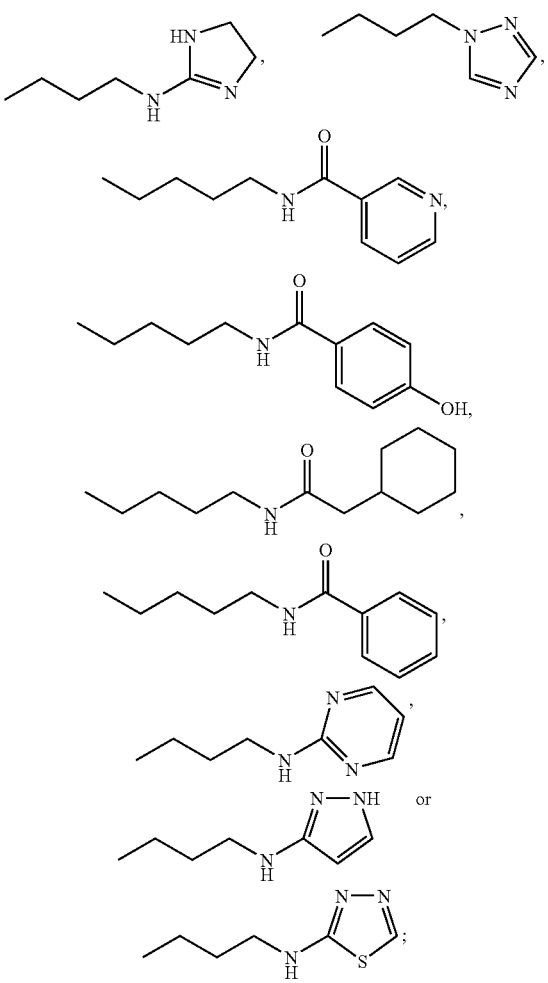

$R_3$ comprises a linker unit and at least one carbocyclic aromatic ring; and $R_x$ comprises from zero to three additional pendant groups;

or an enantiomer, stereoisomer or diastereoisomer thereof, or a pharmaceutically acceptable salt thereof;

and a pharmaceutically acceptable carrier.

2. The method of claim 1 wherein $R_1$ is

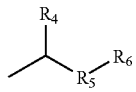

wherein:

$R_4$ is H or =O;

$R_5$ is $(CH_2)_y$, $(CH_2)_y$—O, O or NH, where y is 0 to 4; and $R_6$ is naphthalene selected from the group consisting of:

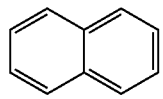 or 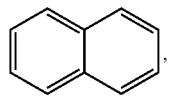, where any available carbon atom of naphthalene forms a bond with $R_5$, if provided, or the adjacent carbon atom with which $R_4$ forms a bond if $R_5$ is not provided.

3. The method of claim 2 wherein $R_6$ is 2-naphthalene.

4. The method of claim 1 wherein the L ring system comprises at least one nitrogen, and $R_3$ forms a bond with the at least one nitrogen.

5. The method of claim 4 wherein $R_3$ is an L- or D-isomer of Phe, Phe(4-F), Phe(4-Br), Phe(4-CF$_3$), Phe(4-Cl), Phe(3-Cl), Phe(2-Cl), Phe(2,4-diCl), Phe(2,4-diF), Phe(3,4-diCl), Phe(5-Cl), Phe(2-Cl,4-Me), Phe(2-Me,4-Cl), Phe(2-F,4-Cl), Phe(4-I), Phe(2,4-diMe), Phe(2-Cl,4-CF$_3$), Phe(3,4-diF), Phe(4-I), Phe(3,4-di-OMe), Phe(4-Me), Phe(4-OMe), Phe(4-NC), or Phe(4-NO$_2$).

6. The method of claim 4 wherein $R_3$ an L- or D-isomer of Phe, Phe(4-F), Phe(4-Br), Phe(4-CF$_3$), Phe(4-Cl), Phe(3-Cl), Phe(2-Cl), Phe(2,4-diCl), Phe(2,4-diF), Phe(3,4-diCl), Phe(5-Cl), Phe(2-Cl,4-Me), Phe(2-Me,4-Cl), Phe(2-F,4-Cl), Phe(4-I), Phe(2,4-diMe), Phe(2-Cl,4-CF$_3$), Phe(3,4-diF), Phe(4-I), Phe(3,4-di-OMe), Phe(4-Me), Phe(4-OMe), Phe(4-NC), or Phe(4-NO$_2$) and an amine capping group.

7. The method of claim 6 wherein the amine capping group is methyl, dimethyl, ethyl, propyl, isopropyl, butyl, isobutyl, pentyl, hexyl, allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7'-amino heptanoyl, 6-Ahx, Amc or 8-Aoc.

8. The method of claim 1 wherein each $R_x$ is independently hydrogen, a $C_1$ to $C_6$ aliphatic linear or branched chain, or a bond or a linker unit comprising from one to nine backbone atoms selected from the group consisting of carbon, sulfur, oxygen and nitrogen and a group comprising at least one aromatic carbocyclic ring.

9. The method of claim 1 wherein L is:

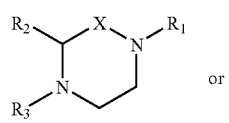 or

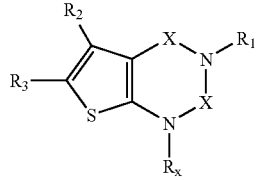

wherein

X is independently $(CH_2)_n$, CH, NH, N, O, C=O, C=S, S, S=O or SO$_2$, the index value n is 0, 1, 2 or 3, and $R_x$ is independently hydrogen, a $C_1$ to $C_6$ aliphatic linear or branched chain, or a bond or a linker unit comprising from one to nine backbone atoms selected from the group consisting of carbon, sulfur, oxygen and nitrogen and a group comprising at least one aromatic carbocyclic ring.

10. A method of claim 1, wherein the melanocortin receptor compound of the formula:

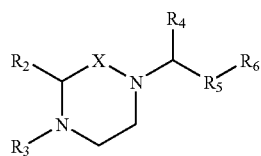

wherein:

$R_2$ is —$(CH_2)_4NH_2$, —$(CH_2)_3NHC(NH_2)$=NH, —$(CH_2)_3$ NHCOCH$_3$, —$(CH_2)_3NHCOOCH_3$, —$(CH_2)_2$ NHC(NH$_2$)=NH, —$(CH_2)_2NHCONH_2$, —$(CH_2)_4$ NHCOH, —$(CH_2)_4NHCOCH_3$, —$(CH_2)_3$ NHCONHCH$_3$, —$(CH_2)_3NHSO_2NH_2$, —$(CH_2)_3$ NHSO$_2$CH$_3$, —$(CH_2)_3NH_2$, —$(CH_2)_3NH(C$=NH$)$ NHMe, —$(CH_2)_3$ NH(C=NH)NHLt, —$(CH_2)_3$NH (C=NH)NHPr, —$(CH_2)_3$NH(C=NH)NHPr-i, —$(CH_2)_3$NH(C=NH)NH$_2$, —$(CH_2)_4$NHCONH$_2$, —$(CH_2)_4$NH(C=NH)NH$_2$,

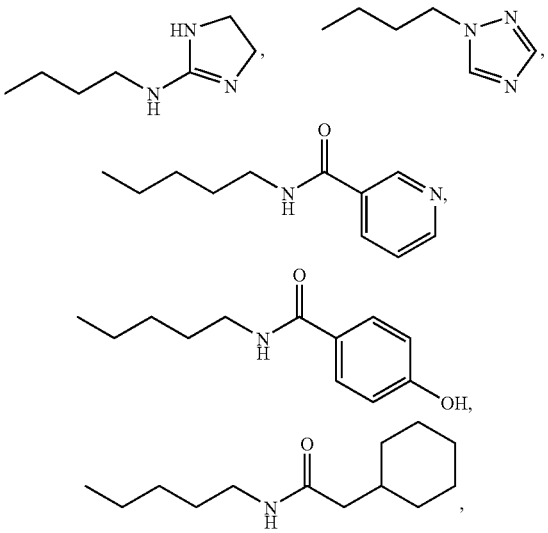

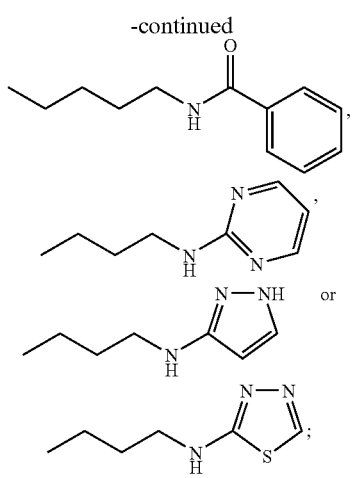

$R_3$ comprises a linker unit and at least one carbocyclic aromatic ring;
$R_4$ is H or =O;
$R_5$ is $(CH_2)_y$, $(CH_2)_y$—O, O or NH, where y is 0 to 4; and
$R_6$ is naphthalene selected from the group consisting of:

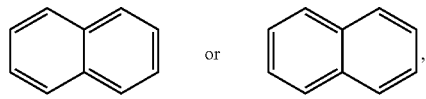

where any available carbon atom of naphthalene forms a bond with $R_5$, if provided, or the adjacent carbon atom with which $R_4$ forms a bond if $R_5$ is not provided;

X is $CH_2$, C=O, C=S, S, S=O or $SO_2$;

or an enantiomer, stereoisomer or diastereoisomer thereof, or a pharmaceutically acceptable salt thereof.

11. The method of claim 10 wherein $R_6$ is 2-naphthalene.

12. The method of claim 10 wherein $R_3$ is a D-isomer of Phe, Phe(4-F), Phe(4-Br), Phe(4-$CF_3$), Phe(4-Cl), Phe(3-Cl), Phe(2-Cl), Phe(2,4-diCl), Phe(2,4-diF), Phe(3,4-diCl), Phe (5-Cl), Phe(2-Cl,4-Me), Phe(2-Me,4-Cl), Phe(2-F,4-Cl), Phe (4-I), Phe(2,4-diMe), Phe(2-Cl,4-$CF_3$), Phe(3,4-diF), Phe(4-I), Phe(3,4-di-OMe), Phe(4-Me), Phe(4-OMe), Phe(4-NC), or Phe(4-$NO_2$).

13. The method of claim 10 wherein $R_3$ a D-isomer of Phe, Phe(4-F), Phe(4-Br), Phe(4-$CF_3$), Phe(4-Cl), Phe(3-Cl), Phe (2-Cl), Phe(2,4-diCl), Phe(2,4-diF), Phe(3,4-diCl), Phe(5-Cl), Phe(2-Cl,4-Me), Phe(2-Me,4-Cl), Phe(2-F,4-Cl), Phe(4-I), Phe(2,4-diMe), Phe(2-Cl,4-$CF_3$), Phe(3,4-diF), Phe(4-I), Phe(3,4-di-OMe), Phe(4-Me), Phe(4-OMe), Phe(4-NC), or Phe(4-$NO_2$) and an amine capping group.

14. The method of claim 13 wherein the amine capping group is methyl, dimethyl, ethyl, propyl, isopropyl, butyl, isobutyl, pentyl, hexyl, allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7'-amino heptanoyl, 6-Ahx, Amc or 8-Aoc.

15. The method of clam 1 wherein the mammal is suffering from obesity.

* * * * *

UNITED STATES PATENT AND TRADEMARK OFFICE
CERTIFICATE OF CORRECTION

PATENT NO. : 7,732,451 B2  
APPLICATION NO. : 11/036282  
DATED : June 8, 2010  
INVENTOR(S) : Shubh D. Sharma et al.

Page 1 of 1

It is certified that error appears in the above-identified patent and that said Letters Patent is hereby corrected as shown below:

Claim 1, Column 34, replace lines 10 through 20 with the following --$R_2$ is -$(CH_2)_4NH_2$, -$(CH_2)_3NHC(NH_2)=NH$, -$(CH_2)_3NHCOCH_3$, -$(CH_2)_3NHCOOCH_3$, -$(CH_2)_2NHC(NH_2)=NH$, -$(CH_2)_2NHCONH_2$, -$(CH_2)_4NHCOH$, -$(CH_2)_4NHCOCH_3$, -$(CH_2)_3NHCONHCH_3$, -$(CH_2)_3NHSO_2NH_2$, -$(CH_2)_3NHSO_2CH_3$, -$(CH_2)_3NH_2$, -$(CH_2)_3NH(C=NH)NHMe$, -$(CH_2)_3NH(C=NH)NHEt$, -$(CH_2)_3NH(C=NH)NHPr$, -$(CH_2)_3NH(C=NH)NHPr-i$, -$(CH_2)_3NH(C=NH)NH_2$, -$(CH_2)_4NHCONH_2$, -$(CH_2)_4NH(C=NH)NH_2$,--.

Claim 2, Column 35, line 17, replace "or" with --and--.

Claim 10, Column 36, replace lines 35 through 44 with the following --$R_2$ is -$(CH_2)_4NH_2$, -$(CH_2)_3NHC(NH_2)=NH$, -$(CH_2)_3NHCOCH_3$, -$(CH_2)_3NHCOOCH_3$, -$(CH_2)_2NHC(NH_2)=NH$, -$(CH_2)_2NHCONH_2$, -$(CH_2)_4NHCOH$, -$(CH_2)_4NHCOCH_3$, -$(CH_2)_3NHCONHCH_3$, -$(CH_2)_3NHSO_2NH_2$, -$(CH_2)_3NHSO_2CH_3$, -$(CH_2)_3NH_2$, -$(CH_2)_3NH(C=NH)NHMe$, -$(CH_2)_3NH(C=NH)NHEt$, -$(CH_2)_3NH(C=NH)NHPr$, -$(CH_2)_3NH(C=NH)NHPr-i$, -$(CH_2)_3NH(C=NH)NH_2$, -$(CH_2)_4NHCONH_2$, -$(CH_2)_4NH(C=NH)NH_2$,--.

Signed and Sealed this

Thirteenth Day of July, 2010

David J. Kappos  
*Director of the United States Patent and Trademark Office*